US010202577B2

(12) United States Patent
Spuhler et al.

(10) Patent No.: US 10,202,577 B2
(45) Date of Patent: Feb. 12, 2019

(54) MICROFLUIDIC SORTING USING HIGH GRADIENT MAGNETIC FIELDS

(71) Applicant: The General Hospital Corporation, Boston, MA (US)

(72) Inventors: Philipp S. Spuhler, Boston, MA (US); Kyle C. Smith, Cambridge, MA (US); Fabio Fachin, Cambridge, MA (US); Thomas Alan Barber, Allston, MA (US); Ravi Kapur, Sharon, MA (US); Mehmet Toner, Charlestown, MA (US); Vincent Pai, Somerville, MA (US); Murat N. Karabacak, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 138 days.

(21) Appl. No.: 15/029,789

(22) PCT Filed: Oct. 20, 2014

(86) PCT No.: PCT/US2014/061405
§ 371 (c)(1),
(2) Date: Apr. 15, 2016

(87) PCT Pub. No.: WO2015/058206
PCT Pub. Date: Apr. 23, 2015

(65) Prior Publication Data
US 2016/0244714 A1 Aug. 25, 2016

Related U.S. Application Data

(60) Provisional application No. 61/892,947, filed on Oct. 18, 2013.

(51) Int. Cl.
*G01N 35/00* (2006.01)
*C12M 1/00* (2006.01)
(Continued)

(52) U.S. Cl.
CPC ....... *C12M 47/04* (2013.01); *B01L 3/502753* (2013.01); *B01L 3/502761* (2013.01);
(Continued)

(58) Field of Classification Search
CPC ............. G01N 35/00; C12M 1/00; B03C 1/01
(Continued)

(56) References Cited

U.S. PATENT DOCUMENTS 5,541,072 A * 7/1996 Wang ................. B03C 1/01
209/214
5,655,665 A * 8/1997 Allen ..................... B03C 1/035
209/223.1
(Continued)

FOREIGN PATENT DOCUMENTS

EP 2615463 7/2013
WO WO 2000/061191 10/2000
(Continued)

OTHER PUBLICATIONS

Han, K.-H. et al, Journal of Applied Physics 2004, 96, 5797-5802.*
(Continued)

*Primary Examiner* — Arlen Soderquist
(74) *Attorney, Agent, or Firm* — Fish & Richardson P.C.

(57) ABSTRACT

Microfluidic devices are described that include a microfluidic channel, a first array of one or more magnets above the microfluidic channel, each magnet in the first array having a magnetic pole orientation opposite to a magnetic pole orientation of an adjacent magnet in the first array, and a second array of one or more magnets beneath the microfluidic channel, each magnet in the second array having a magnetic pole orientation opposite to a magnetic pole orientation of an adjacent magnet in the second array. The first array is aligned with respect to the second array such that magnetic fields emitted by the first array and second array
(Continued)

generate a magnetic flux gradient profile extending through the channel. An absolute value of the profile includes a first maximum and a second maximum that bound a local minimum. The local minimum is located within the microfluidic channel or less than 5 mm away from a wall of the microfluidic channel. Methods of using the new devices are also described.

18 Claims, 21 Drawing Sheets

(51) Int. Cl.
- B03C 1/01 (2006.01)
- G01N 15/14 (2006.01)
- B01L 3/00 (2006.01)
- B03C 1/033 (2006.01)
- B03C 1/28 (2006.01)
- C12M 3/06 (2006.01)
- G01N 15/10 (2006.01)
- G01N 35/10 (2006.01)

(52) U.S. Cl.
CPC ............ B03C 1/01 (2013.01); B03C 1/0332 (2013.01); B03C 1/288 (2013.01); C12M 23/16 (2013.01); G01N 15/1463 (2013.01); G01N 35/0098 (2013.01); B01L 2200/0652 (2013.01); B01L 2300/0816 (2013.01); B01L 2300/0864 (2013.01); B01L 2400/043 (2013.01); B01L 2400/0487 (2013.01); B01L 2400/086 (2013.01); B03C 2201/18 (2013.01); B03C 2201/26 (2013.01); G01N 2015/1006 (2013.01); G01N 2015/149 (2013.01); G01N 2035/00237 (2013.01); G01N 2035/1034 (2013.01)

(58) Field of Classification Search
USPC .......................... 422/502–503; 436/43, 180
See application file for complete search history.

(56) References Cited

U.S. PATENT DOCUMENTS

| | | | |
|---|---|---|---|
| 5,795,470 A | 8/1998 | Wang et al. | |
| 5,968,820 A | 10/1999 | Zborowski et al. | |
| 6,036,857 A * | 3/2000 | Chen ................ | B03C 1/035 209/213 |
| 6,432,630 B1 * | 8/2002 | Blankenstein ......... | B01D 57/02 422/186 |
| 6,540,896 B1 | 4/2003 | Manz et al. | |
| 6,623,984 B1 * | 9/2003 | Fleischman ....... | B01L 3/502715 209/214 |
| 6,767,706 B2 | 7/2004 | Quake et al. | |
| 7,033,473 B2 * | 4/2006 | Gascoyne ................ | B03C 1/00 204/547 |
| 7,807,454 B2 * | 10/2010 | Oh ................... | B01L 3/502761 204/547 |
| 8,021,614 B2 | 9/2011 | Huang et al. | |
| 8,186,913 B2 | 5/2012 | Toner et al. | |
| 8,263,387 B2 * | 9/2012 | Pagano ............ | B01L 3/502761 422/527 |
| 8,268,177 B2 * | 9/2012 | Ying ...................... | B03C 1/002 209/232 |
| 8,551,333 B2 * | 10/2013 | Lin ................... | B01L 3/502761 210/222 |
| 8,689,981 B2 * | 4/2014 | Stone ...................... | B03C 1/288 209/214 |
| 9,220,831 B2 * | 12/2015 | Ingber ................... | A61M 1/36 |
| 9,278,353 B2 * | 3/2016 | Smith ................... | B03C 1/288 |
| 2003/0092029 A1 | 5/2003 | Josephson et al. | |
| 2003/0124194 A1 | 7/2003 | Gaw et al. | |
| 2006/0134599 A1 | 6/2006 | Toner et al. | |
| 2006/0269965 A1 | 11/2006 | Josephson et al. | |
| 2007/0125941 A1 | 6/2007 | Lee et al. | |
| 2008/0124779 A1 * | 5/2008 | Oh .................... | B01L 3/502761 435/173.9 |
| 2009/0047297 A1 * | 2/2009 | Kim ....................... | B03C 1/288 424/184.1 |
| 2009/0053799 A1 * | 2/2009 | Chang-Yen ............... | B03C 1/01 435/287.2 |
| 2010/0044232 A1 * | 2/2010 | Lin .................... | B01L 3/502761 204/660 |
| 2011/0003303 A1 * | 1/2011 | Pagano ............. | B01L 3/502761 435/6.19 |
| 2011/0091987 A1 | 4/2011 | Weissleder et al. | |
| 2012/0080360 A1 * | 4/2012 | Stone ........................ | B03C 1/01 209/214 |
| 2012/0135494 A1 | 5/2012 | Murthy et al. | |
| 2012/0295366 A1 * | 11/2012 | Zilch ................ | B01L 3/502761 436/501 |
| 2013/0189755 A1 * | 7/2013 | Han ....................... | B03C 1/0335 435/173.9 |
| 2013/0217144 A1 | 8/2013 | Rida | |
| 2014/0021105 A1 * | 1/2014 | Lee .................. | G01N 27/44756 209/214 |
| 2015/0336096 A1 * | 11/2015 | Smith ..................... | B03C 1/288 435/309.1 |

FOREIGN PATENT DOCUMENTS

| | | | |
|---|---|---|---|
| WO | WO 2009/132151 | * | 10/2009 |
| WO | WO 2010/121315 | | 10/2010 |
| WO | WO 2014/004577 | | 1/2014 |

OTHER PUBLICATIONS

Han, K.-H. et al, Lab on a Chip 2006, 6, 265-273.*
Adams, J. D. et al, Proceedings of the National Academy of Sciences 2008, 105, 18165-18170.*
Jung, J. et al, Applied Physics Letters 2008, 93, paper 223902, 3 pages.*
Schneider, T. et al, Analyst 2010, 135, 62-70.*
Tsai, S. S. H. et al, Lab on a Chip 2011, 11, 2577-2582.*
Hoshino, K. et al, Lab on a Chip 2011, 11, 3449-3457.*
Forbes, T. P. et al, Lab on a Chip 2012, 12, 1471-1479.*
Ozkumur, E. et al, Science Translational Medicine 2013, 5, paper 179ra47, 11 pages plus supplementary materials.*
Balasubramanian et al., "Multiparameter analysis, including EMT markers, on negatively enriched blood samples from patients with squamous cell carcinoma of the head and neck," PLoS ONE, 2012, 7: e42048.
Berger et al., "Design of a microfabricated magnetic cell separator" Electrophoresis, 2001, 22: 3883-3892.
Bilkenroth et al. ,"Detection and enrichment of disseminated renal carcinoma cells from peripheral blood by immunomagnetic cell separation" Int. J. Cancer, 2001, 92: 577-582.
Carlo et al., "Continuous inertial focusing, ordering, and separation of particles in microchannels," PNAS, 2007, 104: 18892-18897.
Davis et al., "Deterministic hydrodynamics: taking blood apart" PNAS, 2006, 103: 14779-14784.
De Bono et al., "Circulating tumor cells predict survival benefit from treatment in metastatic castration-resistant prostate cancer" Clin. Cancer Res., 2008, 14: 6302-6309.
Extended European Search Report in European Application No. 14853592.5, dated May 3, 2017, 13 pages.
Huang et al., "Continuous Particle Separation Through Deterministic Lateral Displacement," Science, 2004, 304: 987-990.
Iinuma et al., "Detection of tumor cells in blood using CD45 magnetic cell separation followed by nested mutant allele-specific amplification of p53 and K-ras genes in patients with colorectal cancer," Int. J. Cancer, 2000, 89: 337-344.
Inglis et al., "Continuous microfluidic immunomagnetic cell separation," Appl. Phys. Lett., 2004, 85: 5093-5095.
Inglis et al., "Critical particle size for fractionation by deterministic lateral displacement" Lab Chip 2006, 6: 655-658.

(56) References Cited

OTHER PUBLICATIONS

Kalluri et al., "The basics of epithelial-mesenchymal transition," The Journal of Clinical Investigation 2009, 119: 1420-1428.
Karabacak et al., "Microfluidic, marker-free isolation of circulating tumor cells from blood samples," Nature Protocols, 2014, 9(3): 694-710.
Lansdorp et al., "Cyclic tetramolecular complexes of monoclonal antibodies: A new type of cross-linking reagent," Eur. J. Immunol., 1986, 16: 679-683.
Liu et al. "Negative enrichment by immunomagnetic nanobeads for unbiased characterization of circulating tumor cells from peripheral blood of cancer patients," J Transl Med, 2011, 9: 70 (8 pages).
Loutherback et al., "Improved performance of deterministic lateral displacement arrays with triangular posts," Microfluidics Nanofluid, 2010, 7 pages.
Martel et al., "Inertial focusing dynamics in spiral microchannels," Phys. Fluids, 2012, 24: 032001-032001-13.
Martin et al. "Immunomagnetic enrichment of disseminated epithelial tumor cells from peripheral blood by MACS," Experimental Hematology, 1998, 26: 252-264.
Miltenyi, et al., "High gradient magnetic cell separation with MACS," Cytometry, 1990, 11: 231-238.
Münz et al., "Side-by-side analysis of five clinically tested anti-EpCAM monoclonal antibodies," Cancer Cell International, 2010, 10: 44.
Nagrath et al., "Isolation of rare circulating tumour cells in cancer patients by microchip technology," Nature, 2007, 450: 1235-1239.
Ozkumur et al. "Inertial Focusing for Tumor Antigen-Dependent and -Independent Sorting of Rare Circulating Tumor Cells," Science Translational Medicine, 2013, 5: 179ra47-179ra47.
Pamme and Wilhelm, "Continuous sorting of magnetic cells via on-chip free-flow magnetophoresis," Lab Chip, 2006, 6: 974-980.
Partridge et al, "Immunomagnetic separation for enrichment and sensitive detection of disseminated tumour cells in patients with head and neck SCC," J. Pathol., 1999, 189: 368-377.

Stott et al., "Isolation and Characterization of Circulating Tumor Cells from Patients with Localized and Metastatic Prostate Cancer," Science Translational Medicine 2010, 2: 25ra23-25ra23 (11 pages).
Stott et al., "Isolation of circulating tumor cells using a microvortex-generating herringbone-chip," PNAS, 2010, 107: 18392-18397.
Thiery, "Epithelial-mesenchymal transitions in tumour progression," Nat Rev Cancer 2002, 2: 442-454.
Thomas et al., "Specific binding and release of cells from beads using cleavable tetrameric antibody complexes," J. Immunol. Methods, 1989, 120: 221-231.
Tkaczuk et al., "The significance of circulating epithelial cells in Breast Cancer patients by a novel negative selection method," Breast Cancer Res Treat, 2007, 111: 355-364.
Tong et al., "Application of immunomagnetic cell enrichment in combination with RT-PCR for the detection of rare circulating head and neck tumor cells in human peripheral blood," Cytometry, 2007, 72B: 310-323.
Yang et al., "Optimization of an enrichment process for circulating tumor cells from the blood of head and neck cancer patients through depletion of normal cells," Biotechnology and Bioengineering, 2009, 102: 521-534.
Zhang et al., "Binding affinities/avidities of antibody-antigen interactions: Quantification and scale-up implications," Biotechnol. Bioeng., 2006, 95: 812-829.
Zigeuner et al., "Immunomagnetic cell enrichment detects more disseminated cancer cells than immunocytochemistry in vitro," Journal of Urology, Nov. 2000, 164: 1834-1837.
International Search Report and Written Opinion in International Application No. PCT/US14/61405, dated Mar. 24, 2015, 16 pages.
Osman et al., "A Novel Device for Continuous Flow Magnetic Trapping and Sorting of Human Cells Using Flat Micro-Patterned NdFeB Films," *International Conference on Miniaturized Systems for Chemistry and Life Sciences*, 2-6 (2011).
Smistrup et al., "Theoretical analysis of a new, efficient microfluidic magnetic bead separator based on magnetic structures on multiple length scales," *Microfluid Nanofluid*, (2015).

\* cited by examiner

MICROFLUIDIC SORTING USING HIGH GRADIENT MAGNETIC FIELDS

CROSS-REFERENCE TO RELATED APPLICATIONS

This application is a U.S. national stage application under 35 USC § 371 of International Application No. PCT/US2014/061405, filed on Oct. 20, 2014, which claims priority to U.S. Provisional Application No. 61/892,947, filed on Oct. 18, 2013, the entire contents of which are incorporated herein by reference.

TECHNICAL FIELD

The present disclosure relates to microfluidic sorting of analytes using high gradient magnetic fields.

BACKGROUND

Magnetic cell separation is a technique in which magnetic fields are used to isolate cells within a fluid sample. Typically, magnetic particles are selectively attached to one or more desired cells using antibodies that bind to the cell surface. Cells having the attached magnetic particles then can be confined or deflected within a microfluidic device using an applied magnetic field to isolate the magnetically labeled cells from other analytes in the fluid sample. In some instances, the flow velocities, and thus the shear forces exerted on the cells, approach zero near the fluid channel walls of the device. This can result in the cells binding non-specifically to the walls, such that the cells aggregate, e.g., in the form of plaques on the walls. When large sample volumes are processed such plaque aggregation limits the sample volume that can be processed. In addition to clogging the device, the plaque aggregates can disrupt microfluidic device operation when large chunks of plaque break off ("burp") from the primary plaque aggregate on the channel wall. These chunks of plaque can contain hundreds or thousands cells and their behavior in the microfluidic device may be unpredictable and difficult to control.

SUMMARY

The present disclosure is related to sorting magnetic, e.g., magnetically labeled, particles in microfluidic channels using high gradient magnetic fields arranged to help avoid aggregation of the particles near walls of the microfluidic channels. In general, one aspect of the present disclosure can be embodied in microfluidic devices that employ high magnetic field gradients for sorting target particles, e.g., agents or analytes (e.g., nucleic acids, polypeptides, bacteria, and cells) flowing within a microfluidic channel of the device. The devices can include a first array of one, two, or more magnets arranged above the microfluidic channel, and a second array of one, two, or more magnets arranged beneath the channel. The first and second arrays of magnets produce magnetic fields that combine to generate a magnetic flux gradient profile that extends through the microfluidic channel. An absolute value of the magnetic flux gradient profile has a first peak and a second peak that bound a local minimum. The absolute of the gradient between each peak and the local minimum gives rise to a strong magnetic force that can "pull" magnetically labeled particles traveling within the microfluidic channel from the particle's initial trajectory. Depending on the positioning of the gradient profile, aggregation of the magnetically labeled particles near the microfluidic channel walls can be avoided.

In general, in a first aspect, the subject matter of the present disclosure can be embodied or implemented in microfluidic devices that include a microfluidic channel, a first array of one, two, or more magnets arranged above the microfluidic channel, each magnet in the first array has a magnetic pole orientation that is opposite to a magnetic pole orientation of an adjacent magnet in the first array, and a second array of one, two, or more magnets arranged beneath the microfluidic channel, each magnet in the second array has a magnetic pole orientation that is opposite to a magnetic pole orientation of an adjacent magnet in the second array. The first array is aligned with respect to the second array such that magnetic fields emitted by the first array and the second array together generate a magnetic flux gradient profile that extends through the microfluidic channel, and an absolute value of the magnetic flux gradient profile includes a first maximum and a second maximum that bound a local minimum in the magnetic flux gradient profile. The local minimum is located within the microfluidic channel or less than 5 mm away from a wall of the microfluidic channel (e.g., outside the channel).

The microfluidic devices can include one or more of the following features in any combination. For example, in some implementations, a value of the local minimum is 0.0 T/m or about 0.0 T/m. In some implementations, the magnetic flux gradient profile extends transverse to a central longitudinal axis of the microfluidic channel.

In some implementations, a distance between the first maximum and the second maximum is less than 5 mm. The distance between the first maximum and the second maximum can be less than 1 mm, less than 500 μm, or less than 100 μm.

In some implementations, each of the first maximum and the second maximum in the absolute value of the magnetic flux gradient is at least 50 T/m. Each of the first maximum and the second maximum in the absolute value of the magnetic flux gradient can be at least 400 T/m, at least 500 T/m, at least 600 T/m, at least 700 T/m, at least 800 T/m, at least 900 T/m, or at least 1000 T/m.

In certain implementations, a first interface between two magnets in the first array is substantially aligned with a second interface between two magnets in the second array.

In some implementations, a distance between the first array and the second array is less than 10 mm. The distance between the first array and the second array can be less than 5 mm, less than 2 mm, or less than 1 mm.

In some implementations, the device further includes a substrate between the microfluidic channel and the second array, in which a first surface of the substrate forms a floor to the microfluidic channel. The substrate can include glass. The device can include a cover layer on the first surface of the substrate, in which the cover layer defines walls of the microfluidic channel. The cover layer can include polydimethylsiloxane (PDMS). The first array can be positioned on a surface of the cover layer, and the second array can be positioned on a second surface of the substrate.

In certain implementations, each magnet in the first array has a magnetic pole orientation that is opposite to a magnetic pole orientation of a corresponding magnet in the second array.

In some implementations, at least one of the first maximum in the magnetic flux gradient and the second maximum in the magnetic flux gradient occurs within the microfluidic channel. In some implementations, both the first maximum in the magnetic flux gradient and the second maximum in the magnetic flux gradient occur within the microfluidic channel.

In some implementations, the first array includes more than two magnets, the second array includes more than two magnets, and the absolute value of the magnetic flux gradient profile includes at least two local minima, in which at least one of the local minima is located within the microfluidic channel.

In certain implementations, the microfluidic channel is a first microfluidic channel, in which the device further includes a second microfluidic channel arranged adjacent to the first microfluidic channel, and the magnetic flux gradient profile extends through both the first microfluidic channel and the second microfluidic channel. The second microfluidic channel can be in fluid communication with the first microfluidic channel.

In some implementations, the device includes an inertial focusing region fluidly coupled to an input of the microfluidic channel, in which the inertial focusing region is configured to focus particles within a fluid sample to one or more common fluid streamlines.

In some implementations, the device further includes a hydrodynamic particle sorting region fluidly coupled to the microfluidic channel, in which the hydrodynamic particle sorting region is configured to sort particles based on particle size.

In certain implementations, the device includes a waste channel fluidly coupled to an output of the microfluidic channel, and a target channel fluidly coupled to the output of the microfluidic channel, in which the local minimum is aligned with a longitudinal axis of the waste channel.

In some implementations, the device includes two separate inertial focusing regions fluidly coupled to an input of the microfluidic channel, in which each inertial focusing region is configured to focus particles within a fluid sample to a corresponding common streamline, and the two inertial focusing regions are coupled to a common sample input port.

In some implementations, either one or both of the first maximum and second maximum are located within the channel.

In certain implementations, the local minimum is in a fluid passageway of the microfluidic channel. The local minimum can be greater than or equal to a distance of 100 µm away from the wall of the microfluidic channel.

In another aspect, the subject matter of the present disclosure can be embodied or implemented in methods of sorting target particles, e.g., agents or analytes, using the microfluidic devices described herein, in which the methods include flowing a fluid sample through the microfluidic channel, the fluid sample including the target analyte and one or more magnetic particles, and exposing, during operation of the microfluidic device, the fluid sample to the magnetic flux gradient profile, in which the magnetic flux gradient deflects the one or more magnetic particles toward the local minimum.

The methods can include one or more of the following features in any combination. For example, the fluid sample can include one or more waste particles in addition to the target analyte, and the one or more magnetic particles can be bound to the one or more waste particles such that the magnetic flux gradient deflects the waste particles with the one or more magnetic particles away from an initial fluid flow trajectory of the fluid sample without deflecting the target analyte. The methods can further include collecting the target analyte from the fluid flow trajectory at an output of the microfluidic channel subsequent to the deflection of the one or more waste particles.

In some implementations, the one or more magnetic particles are bound to the target analyte such that the magnetic flux gradient deflects the target analyte with the one or more magnetic particles away from an initial fluid flow trajectory of the fluid sample, and the method further includes collecting the target analyte at an output of the microfluidic channel.

In some implementations, the one or more magnetic particles are selected from the group consisting of superparamagnetic beads, paramagnetic beads, diamagnetic beads, ferromagnetic beads, and combinations thereof. The one or more magnetic particles can have diameters less than or equal to approximately 0.5 µm, e.g., less than or equal to approximately 0.1 µm. The one or more magnetic particles each can have a magnetic moment less than or equal to approximately 35 kA/m.

In another aspect, the subject matter of the present disclosure can be embodied in methods of sorting analytes in a microfluidic device, in which the microfluidic device includes a magnetophoresis region. The methods include flowing a fluid sample containing a mixture of a first multiple of analytes and a second multiple of analytes into the magnetophoresis region, the second multiple of analytes being bound to magnetic particles. A magnetic flux gradient profile within the magnetophoresis region deflects the second multiple of analytes from the fluid sample, in which an absolute value of the magnetic flux gradient profile includes a first maximum and a second maximum that bound a local minimum in the magnetic flux gradient profile, and in which the local minimum is located within the microfluidic channel in the magnetophoresis region or less than 5 mm from a microfluidic channel wall in the magnetophoresis region.

The methods can include one or more of the following features in any combination. For example, the microfluidic device can further include a hydrodynamic particle sorting region arranged upstream from and in fluid communication with the magnetophoresis region. The method can further include: prior to flowing the fluid sample into the magnetophoresis region, introducing the fluid sample into the hydrodynamic particle sorting region to separate a first portion of the first analytes from the fluid sample, in which the remaining fluid sample from the hydrodynamic sorting region is passed to the magnetophoresis region. The microfluidic device can further include an inertial focusing region arranged upstream from and in fluid communication with the magnetophoresis region, and the method can further include prior to flowing the fluid sample into the magnetophoresis region, flowing the remaining fluid sample from the hydrodynamic region into the inertial focusing region, in which the inertial focusing region focuses analytes in the remaining fluid sample into one or more common streamlines.

In some implementations, the magnetic flux gradient profile within the magnetophoresis region deflects the second multiple of analytes from the one or more common streamlines. The method can further include collecting, at an output of the magnetophoresis region, a second portion of the first multiple of analytes from the one or more common streamlines after deflection of the second multiple of analytes.

In some implementations, the microfluidic device further includes an inertial focusing region arranged upstream from and in fluid communication with the magnetophoresis region, and the method further includes: prior to flowing the fluid sample into the magnetophoresis region, introducing the fluid sample into the inertial focusing region, in which the inertial focusing region focuses analytes in the fluid sample into one or more common streamlines.

In some implementations, the first multiple of analytes is not bound to magnetic particles.

In some implementations, the local minimum is located at a distance of greater than or equal to about 100 µm from the microfluidic channel wall. In some implementations, the local minimum is located substantially at a center of the microfluidic channel.

In some implementations, the microfluidic devices further include one or more first inertial focusing region, e.g., a first and a second inertial focusing region, in which each inertial focusing region is fluidly coupled to a common input port of the magnetophoresis region, and the method further includes: flowing a first fluid sample portion into the first inertial focusing region, in which the first inertial focusing region focuses analytes in the first fluid sample portion into a first streamline; and flowing a second fluid sample portion into the second inertial focusing region, in which the second inertial focusing region focuses analytes in the second fluid sample portion into a second streamline, in which both the first and second streamlines enter the common input port of the magnetophoresis region.

In some implementations, the magnetic flux gradient profile within the magnetophoresis region deflects the second multiple of analytes from the first and second fluid streamlines into a separate third fluid streamline.

In some implementations, the methods further include, subsequent to deflecting the second multiple of analytes: directing the first, second, and third fluid streamlines to first, second, and third output channels, respectively; collecting, at the first and second output channels, the first multiple of analytes; and collecting, at the third output channel, the second multiple of analytes.

In another aspect, the subject matter of the present disclosure can be embodied in methods of sorting analytes in a microfluidic device including a first microfluidic channel arranged in fluid communication with a second microfluidic channel, in which a magnetic flux gradient extends through both the first and second microfluidic channels, where the method includes introducing a fluid sample containing a first multiple of analytes into the first microfluidic channel. The first multiple of analytes are bound to magnetic particles, and the magnetic flux gradient profile within the first microfluidic channel deflects a first portion of the first multiple of analytes from the fluid sample. The method further includes flowing a remaining fluid sample from the first microfluidic channel into the second microfluidic channel, in which the magnetic gradient profile deflects a second portion of the first multiple of analytes from the remaining fluid sample, and in which the absolute value of the magnetic flux gradient profile includes a first maximum and a second maximum that bound a local minimum in the magnetic flux gradient profile, the local minimum being located within one of the first microfluidic channel or the second microfluidic channel, and in which either the first maximum or the second maximum is located within the other one of the first microfluidic channel or the second microfluidic channel.

The methods can include one or more of the following features in any combination. For example, the method can further include collecting the first portion of the first multiple of analytes at an output of the first microfluidic channel. In some implementations, the remaining fluid sample includes a second multiple of analytes that are not bound to magnetic particles, and the method further includes: collecting the second multiple of analytes at a first output of the second microfluidic channel; and collecting the second portion of the first multiple of analytes at a second output of the second microfluidic channel.

In some implementations, the microfluidic devices further include one or more inertial focusing regions, e.g., a first inertial focusing region, upstream from and fluidly coupled to an input of the first microfluidic channel, and the methods further include: introducing the fluid sample into the first inertial focusing region prior to introducing the fluid sample into the first microfluidic channel, in which the first inertial focusing region focuses analytes in the first portion of the fluid sample portion into a first streamline that enters the first microfluidic channel.

In some implementations, the microfluidic devices include a second inertial focusing region fluidly coupled to an output of the first microfluidic channel and fluidly coupled to an input of the second microfluidic channel, in which the second inertial focusing region focuses analytes in the remaining fluid sample into a second streamline, and in which the magnetic gradient profile deflects the second portion of the first multiple of analytes from the second streamline.

In yet another aspect, the subject matter of the present disclosure can be embodied or implemented in microfluidic devices that include a microfluidic channel; a first magnet arranged above the microfluidic channel; and a second magnet arranged beneath the microfluidic channel, wherein the first magnet has a polarization orientation that is opposite to a polarization orientation of the second magnet, the first magnet is aligned with respect to the second magnet such that magnetic fields emitted by the first magnet and the second magnet together generate a magnetic flux gradient profile that extends through the microfluidic channel, wherein an absolute value of the magnetic flux gradient profile includes a first maximum and a second maximum that bound a local minimum in the magnetic flux gradient profile, and the local minimum is located within the microfluidic channel or less than 5 mm away from, e.g., outside of, a wall of the microfluidic channel.

As used herein, "specifically binds" means that one molecule, such as a binding moiety, e.g., an oligonucleotide or an antibody, binds preferentially to another molecule, such as a target molecule, e.g., a nucleic acid or protein, in the presence of other molecules in a sample.

As used herein, "magnetic moment" is the tendency of a magnetic material to align with a magnetic field.

As used herein, a "magnetizable particle" is understood to mean either a magnetic particle or a non-magnetic analyte bound to a magnetic particle.

Implementations of the subject matter described herein provide several advantages. For example, by configuring the local minimum in the magnetic flux gradient profile to be located away from the microfluidic channel walls (e.g., near the center of the microfluidic channel), it is possible to reduce or eliminate the formation of plaques on the channel walls, which could otherwise clog the microfluidic channels. In some implementations, the use of inertial focusing in combination with magnetophoresis enhances the efficiency with which magnetic or magnetizable particles can be isolated from unlabeled or non-magnetically labeled particles. In addition, using inertial focusing allows the magnetic or magnetizable particles to be laterally aligned in a microfluidic channel with a desired position of the magnetic flux gradient, such as the position where the magnetic flux gradient is highest or lowest. Combining multiple inertial focused streams into a single channel where magnetophoresis occurs can, in certain instances, improve the throughput of analyte separation and isolation. Furthermore, by using multiple magnetophoresis stages in series, it is possible to improve the efficiency with which targeted analytes are isolated from a fluid sample.

Unless otherwise defined, all technical and scientific terms used herein have the same meaning as commonly understood by one of ordinary skill in the art to which this invention belongs. Although methods, materials, and devices similar or equivalent to those described herein can be used in the practice or testing of the present invention, suitable methods, materials and devices are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
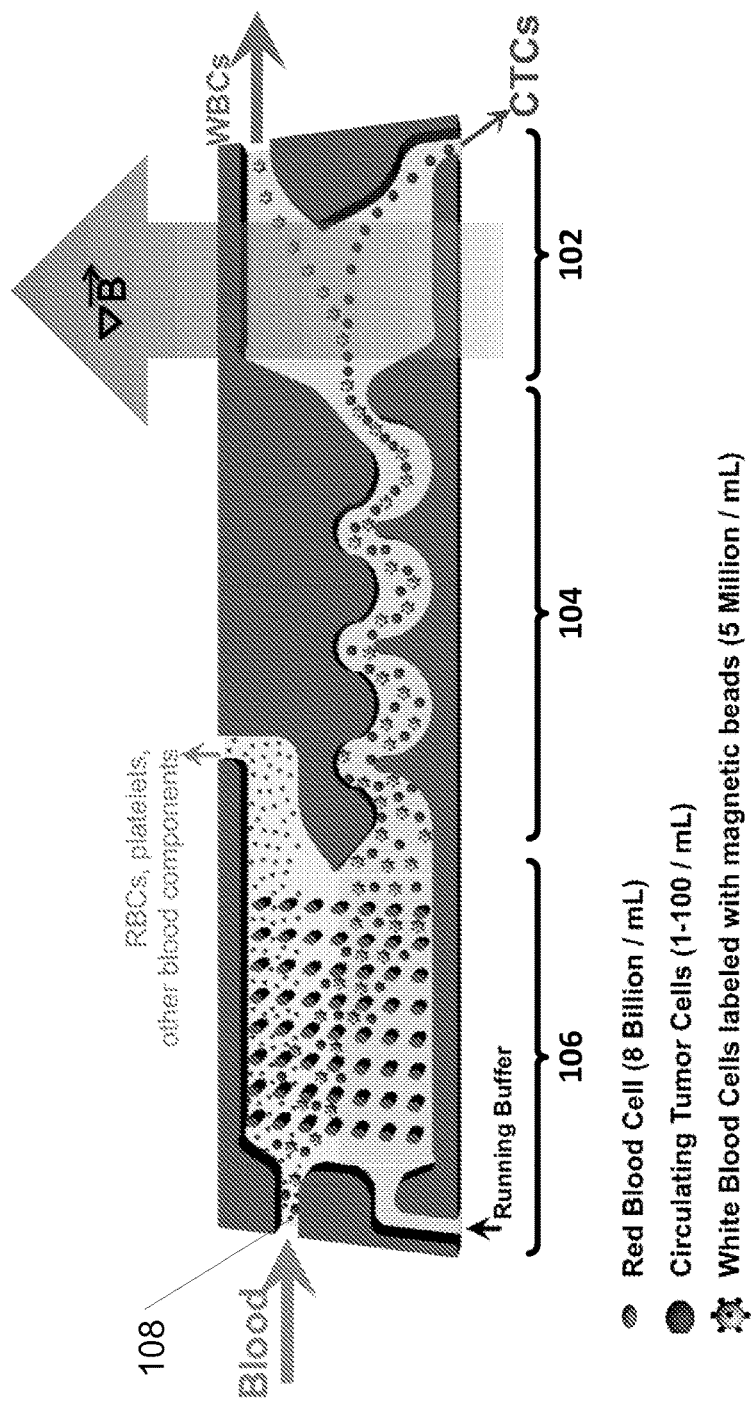
FIG. 1 is a schematic illustrating an example of a microfluidic system.

FIG. 1 is a schematic illustrating an example of a microfluidic system 100 that is capable of sorting particles, in part by using magnetic fields having high magnetic flux gradients. The system 100 includes three sections arranged in series and fluidly coupled to one another: a magnetophoresis region 102, an optional inertial focusing region 104, and an optional hydrodynamic particle sorting region 106. In the present example, a fluid sample (e.g., blood, e.g., whole or diluted blood) is provided to an input port 108 of the hydrodynamic sorting region 106. The sample may contain multiple analytes, some of which are specifically bound to magnetic particles. For example, the sample may include whole blood incubated with magnetic beads that specifically bind to white blood cells within the sample. As the sample flows through the hydrodynamic cell sorting region 106, certain constituents of the sample (e.g., small components such as red blood cells, platelets, and other blood components) are removed by the cell sorter 106. A technique to sort the particles includes providing an array of posts having a pillar size and array offset designed to deflect particles above a certain size, thereby separating them from the main suspension.

The remaining sample containing larger analytes (e.g., nucleated cells such as circulating tumor cells and the white blood cells that are specifically bound to magnetic beads) flows into the inertial focusing region 104, where the analytes are focused into a common streamline. The inertial focusing region 104 aligns the remaining sample components using inertial forces to enable their precise lateral positioning. Further details on the hydrodynamic sorting region 106 and the inertial focusing region 104 are described below.

The narrowed streamlines containing the remaining particles from the inertial focusing region 104 then pass into a microfluidic channel in the magnetophoresis region 102. Magnetophoresis refers to the process of inducing motion on a magnetizable particle in a fluid by applying a magnetic flux gradient $\nabla\vec{\nabla B}$. The force on a magnetizable particle passing through the channel is proportional to the magnitude of $\nabla\vec{B}$, where $\nabla$ corresponds to the vector differential operator and B is the magnetic flux. The deflection allows isolation and capture of both the magnetically labeled analytes and the non-labeled analytes. To avoid the accumulation of cells into plaques, the magnetophoresis region 102 can be configured to produce a magnetic field profile that deflects the magnetically labeled analytes toward a position sufficiently far enough away from the channel walls, such that the analytes cannot bind to the walls.

Magnetophoresis

Figure 2A:
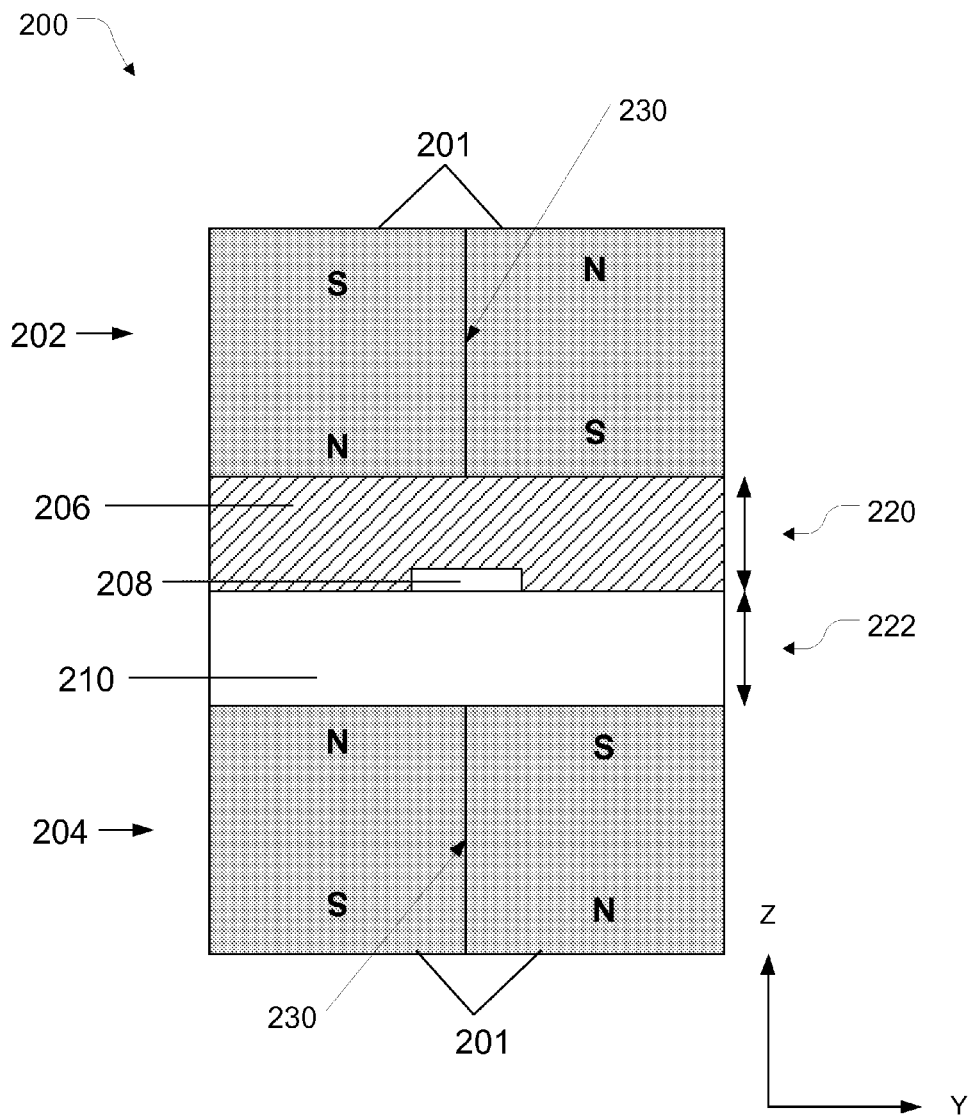
FIG. 2A is a schematic that illustrates a cross-section view of an example of a microfluidic device.

FIG. 2A is a schematic that illustrates a cross-section view of an example of a microfluidic device 200 capable of generating high magnetic gradients for isolating target analytes. The device 200 can be used, for example, as the magnetophoresis region of a microfluidic system, such as the system 100 shown in FIG. 1. A Cartesian coordinate system is provided for reference, in which the positive x-direction is into the page. The device 200 includes a first array 202 of two or more magnets 201, and a second array 204 of two or more magnets 201. The first array 202 is arranged on top of a microfluidic channel cover 206 that defines a microfluidic channel region 208 through which a sample fluid can flow. The second array 204 of magnets is arranged beneath the substrate 210.

The arrangement of magnets shown in FIG. 2A is called a "quadrupole" configuration and establishes an overall magnetic flux that passes through the device 200, including the channel region 208. As shown in FIG. 2A, the "north" magnetic pole of each magnet is labeled "N" and the "south" magnetic pole of each magnet is labeled "S." Each magnet 201 has a magnetic pole orientation that is opposite to a magnetic pole orientation of an adjacent magnet in its array. Furthermore, the magnetic pole orientation of each magnet in an array is also opposite to a corresponding magnet in the other array. That is, each magnet orientation in an array is aligned so that it faces a different magnet orientation in the opposite array. The interface 230 between the two magnets in the top array 202 is also aligned with the interface 230 between the two magnets in the bottom array 204. For example, in the schematic of FIG. 2A, the interface 230 between the two magnets in the top array 202 is aligned along the z-direction with the interface 230 between the two magnets in the bottom array 204.

Some misalignment between the magnet interface of the first array and the magnet interface of the second array is allowable. Because the zero-point in the flux gradient occurs at a position corresponding to an average of the interface positions, some misalignment of the arrays relative to one another (e.g., a misalignment of 300 microns) does not substantially distort the resulting flux gradient profile.

Figure 2B:
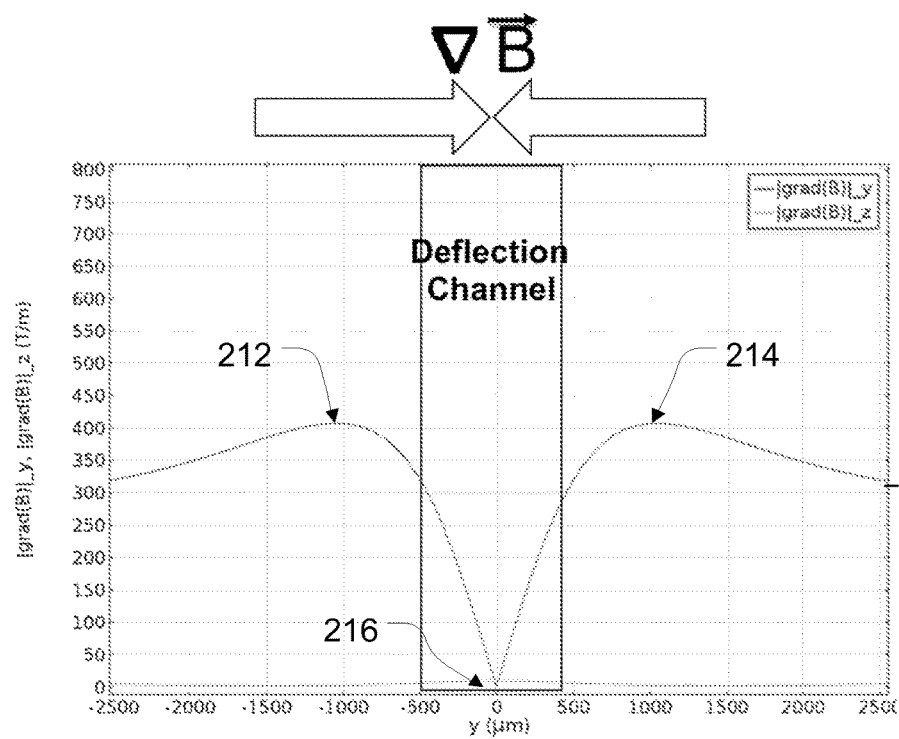
FIG. 2B is a plot that shows a simulation of the magnitude of a magnetic flux gradient profile for the quadrupole configuration of FIG. 2A, in which the separation between the first and second magnet array is 2 mm.

As explained above, the force on a magnetic particle flowing through the channel 208 is proportional to the magnitude of $\nabla B$, i.e., the magnetic flux gradient. FIG. 2B is a plot that shows a simulation of the magnitude (i.e., absolute value) of the magnetic flux gradient profile for the quadrupole configuration of FIG. 2A. The flux profile extends along the y direction and, for the purposes of this example, is assumed to uniformly extend into and out of the page. Additionally, there is negligible flux gradient along the z-direction. The region identified as "Deflection Channel" in FIG. 2B represents the boundary of the microfluidic channel superimposed on the flux gradient profile. As shown in FIG. 2B, the magnetic flux gradient profile includes two points 212, 214 of maximum magnitude (approximately 400 T/m) that bound a local minimum, 216. The values shown represent the magnitude of the gradient, and thus are proportional to the extent of the magnetic force. However, the direction of the magnetic force is determined by the sign of $\nabla\vec{B}$. In the present case, the sign of $\nabla\vec{B}$ is positive to the left of the channel center (i.e., y=0 μm) and the direction of the magnetic force on that side of the channel is toward the right in FIG. 2B. In contrast, the sign of $\nabla\vec{B}$ is negative to the right of the channel center, and the direction of the magnetic force on that side of the channel is toward the left in FIG. 2B. Accordingly, magnetizable particles traveling through the channel experience a large force in both the positive and negative y-direction (as indicated by the arrows in FIG. 2B) toward a local minimum in $\nabla\vec{B}$ at the center of the channel. Assuming the force is large enough, the particles can be deflected to the channel position corresponding to the local minimum in $\nabla\vec{B}$. Because the magnetizable particles experience opposing lateral forces as they propagate through the channel, the particles can be maintained in a narrow region within the channel, and may not substantially stray from that region. For this reason, the position of the local minimum in the gradient flux profile is also called the "focus position."

FIG. 2A shows that the magnets in each array are arranged so that adjacent magnets are in direct contact. However, it is not necessary that adjacent magnets be touching one another. Instead, adjacent magnets can be separated by a certain distance and still establish the desired magnetic flux gradient profile. For example, adjacent magnets in an array can be separated by a distance of up to about 0.5 mm, such as about 0.1 mm, 0.2 mm, 0.3 mm, or 0.4 mm. In such cases, the "interface" between two adjacent magnets corresponds to the plane in the gap (or a non-magnetic spacer) that is equidistant between the magnets (e.g., extending along the x-z plane in FIG. 2A).

In the present example, the local minimum is located at the center of the channel due to the alignment of the first and second magnet arrays (i.e., the interface between the first and second magnet in the first array is aligned with the interface between the first and second magnet in the second array). However, by changing the position of the microfluidic channel with respect to the magnet arrays (or vice versa), it is possible to focus magnetic particles (or magnetically labeled particles) to any desired lateral position along the channel. In the configuration shown in FIG. 2A, the center of the microfluidic channel 208 is aligned to the position where the gradient in magnetic flux reaches zero (i.e., the focus position). As a result, magnetic particles that flow through the channel 208 would be deflected to the channel center.

In the case that the magnetic particles are bound, specifically or otherwise, to cells or other analytes (i.e., "magnetically labeled analytes") within a fluid sample, the magnetic flux gradient profile can be used to focus the analytes away from the channel walls and prevent the formation of plaques. Alternatively, or in addition, the orientation of the channel with respect to the flux gradient profile can be configured such that the magnetically labeled analytes are deflected away from an initial fluid trajectory. Non-magnetic particles and analytes are unaffected by the magnetic force and continue flowing with the sample along approximately the same initial trajectory. The separation of the magnetically labeled analytes enables independent collection of one or both of the labeled and non-labeled analytes. In contrast to a device in which a homogeneous magnetic field extends throughout the fluidic channel, the magnetic flux gradient enables, in certain implementations, a greater "pull" on magnetic particles, thus allowing quicker isolation of magnetically labeled analytes from other analytes in the fluid sample. As a result, higher sample fluid velocities and/or shorter fluidic channels lengths can be used for separating the target analytes.

The deflection and isolation of magnetically labeled analytes that one desires to collect from undesired analytes in a fluid sample is referred to as "positive selection." In contrast, the deflection of magnetically labeled analytes that are considered waste to isolate non-magnetically labeled particles, is referred to as "negative selection" or "depletion." Either technique can be employed with the devices disclosed herein.

The high flux gradients that are obtainable with the devices described herein have several advantages. For example, in some implementations, the high flux gradients enable the isolation of target analytes bound to magnetic particles having very low magnetic moments: the high magnetic force in the microfluidic channel exerts a greater "pull" on the magnetic particles having low magnetic moments. Alternatively, or in addition, the high flux gradients enable the isolation of target analytes bound to a lower number of magnetic particles, because the magnetic force is high, fewer magnetic particles having a particular magnetic moment are required to be bound to a target analyte.

In some implementations, the high flux gradient enables magnetically labeled analytes to be separated/isolated at high flow rates (e.g., at least approximately 50 μL/min, at least approximately 100 μL/min, at least approximately 150 μL/min, at least approximately 300 μL/min, at least approximately 500 μL/min, or at least approximately 1000 μL/min), thus increasing the efficiency with which the device can be used for detection and separation of target analytes.

In some implementations, the high flux gradients enable the use of shorter microfluidic channels/isolation regions (e.g., less than approximately 150 mm, less than approximately 100 mm, less than approximately 50 mm, less than approximately 10 mm, or about approximately 1 mm) since magnetically labeled analytes can be separated over much shorter distances.

The maximum gradient generated by the device can be varied. For example, the array can be configured to provide a maximum flux gradient magnitude in the range of about 1500 T/m to about 300 T/m. More particularly, the value can be in the range of about 1000 T/m to about 500 T/m. The maximum flux gradient magnitude can be modified based on one or more parameters of the microfluidic device 200 including, for example, the strength of the magnet(s) that emits the magnetic field. The stronger the magnet used, the greater the flux gradient that can be achieved. The strength of the maximum magnetic field that can be produced from a magnet is denoted using the symbol Br, i.e., the remanent magnetization of the magnet. The types of magnets that may be used include, for example, permanent magnets or electromagnets. The magnets may be composed of material including, for example, alloys of NdFeB, SmCo, AlNiCo, or ferrite. The magnetic field provided by the magnets may be in the range of approximately 0.001 T to approximately 1.5 T. For example, the magnetic field emitted by the one or more magnets 102 may be approximately 0.1 T, approximately 0.3 T, approximately 0.5 T, approximately 1 T, or approximately 1.3 T. Other values for the magnetic field are possible as well.

Figure 2C:
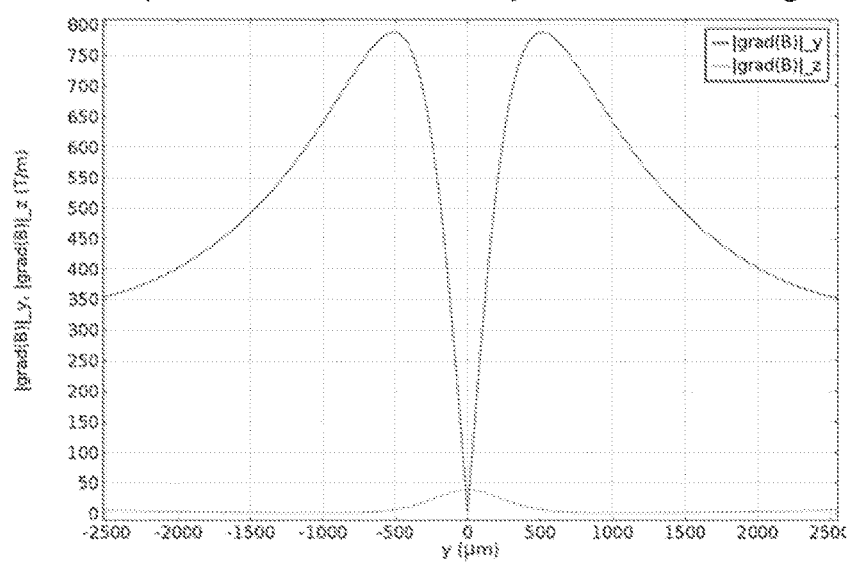
FIG. 2C is a plot that shows a simulation of the magnitude of a magnetic flux gradient profile for the quadrupole configuration of FIG. 2A, in which the separation between the first and second magnet array is 1 mm.

Another parameter that affects the flux gradient profile is the size of the separation between the top array of magnets and the bottom array of magnets. Altering this separation height modifies not only magnitude of the flux gradient, but also the distance between the points of maximum flux gradient. The spacing between the magnets can be adjusted by modifying the height of the microfluidic channel cover 206 and the thickness of the substrate 210. In the example shown in FIG. 2A, the channel cover 206 has a height 220 of about 1 mm, measured as the distance between the substrate 210 and the first array 202 of magnets along the z-direction. The substrate 210 also has a thickness 222, measured as the distance from the bottom array 204 to the channel cover 208 along the z-direction, of about 1 mm. As shown in FIG. 2B, this corresponds to a maximum magnetic flux of about 400 T/m. FIG. 2C is a plot illustrating a simulation of the magnitude of the magnetic flux gradient across the channel 208 for the same device, except that the height 220 of the cover channel 208 and the thickness 222 of the substrate 210 have both been reduced to about 0.5 mm. As shown in the plot of FIG. 2C, the smaller separation between the magnet arrays results in a much higher maximum in the magnetic flux gradient, i.e., about 800 T/m. Moreover, the distance between the first maximum and the second maximum in the flux gradient has narrowed. As a result, magnetizable particles can be focused to a much narrower region within the fluid channel 208.

In general, the "focus position" refers to the lateral extent of a channel through which a collection of particles passes in response to the magnetic flux gradient. In some implementations, particles can be localized within a length of the channel having a width of, at most, 1.05, 2, 3, 4, or 5 times the width of the particles. In some implementations, the distance between the first maximum and the second maximum in the flux gradient can be configured to be between about 10 μm to about 10 mm. For example, the distance between the first maximum and the second in the flux gradient can be about 100 μm, about 500 μm, about 1 mm, about 2 mm, about 4 mm, about 6 mm, or about 8 mm. Other distances are possible as well.

The height of the cover channel 208 is the extent of the opening of the channel 208 as measured along the z-direction (see FIG. 2A). The height of the cover channel 208 can fall within the range of approximately 10 nm to approximately 10 mm. For example, the height of the cover channel 208 can be approximately 100 nm, 1 μm, 10 μm, 100 μm, 500 μm, 750 μm, 1 mm, 5 mm, or 9 mm. Other heights are possible as well.

Similarly, the thickness of the substrate 210 can fall within the range of approximately 500 μm to approximately 10 mm. For example, the thickness of the substrate 210 can be 600 μm, 750 μm, 900 μm, 1 mm, 2 mm, 3 mm, 4 mm, 5 mm, 6 mm, 7 mm, 8 mm, or 9 mm. Other thicknesses are possible as well. The microfluidic channel 208 can have a cross-sectional area that falls within the range of about 250 μm$^2$ to about 10$^6$ μm$^2$. The width of the channel (e.g., as measured along the y-axis in FIG. 2A) can be in the range of about 100 μm to about 5 mm. For example, the channel width can be about 500 μm, about 1 mm, about 2 mm, about 3 mm, or about 4 mm. The height of the channel (e.g., as measured along the z-axis in FIG. 2A) can be in the range of 50 μm to about 2 mm. For example, the height can be about 100 µm, about 250 µm, about 500 µm, about 750 µm, about 1 mm, or about 1.5 mm.

The microfluidic cover 206 can be formed from any applicable material that is compatible with the fluid sample to be delivered through the microfluidic channel. For example, the microfluidic cover 206 can be formed of glass, silicon, polydimethylsiloxane (PDMS), polymethylmethacrylate (PMMA), cyclo olefin polymer (COP), polycarbonate, polyimide, or other suitable material. The substrate 210 may be formed of a low magnetic permeability material, e.g., a non-magnetic material including, for example, glass or any of a wide variety of plastics.

In the example shown in FIG. 2B, the magnetic flux gradient profile is oriented such that it extends transverse to a central longitudinal axis (i.e., an axis centered in the channel and extending along the x-direction into and out of the page) of the microfluidic channel 208. In other implementations, the magnet arrays can be arranged such that the magnetic flux gradient profile is oriented at an oblique angle with respect to the central longitudinal axis of the microfluidic channel. This allows magnetizable particles to be deflected along pathways that are non-parallel with the microfluidic channel. Since the local minimum in the flux gradient profile aligns with the interface between the magnets in the arrays, the orientation of the flux gradient profile can be altered by arranging the interface between the magnets to be oblique to the central longitudinal axis of the microfluidic channel.

Figure 3:
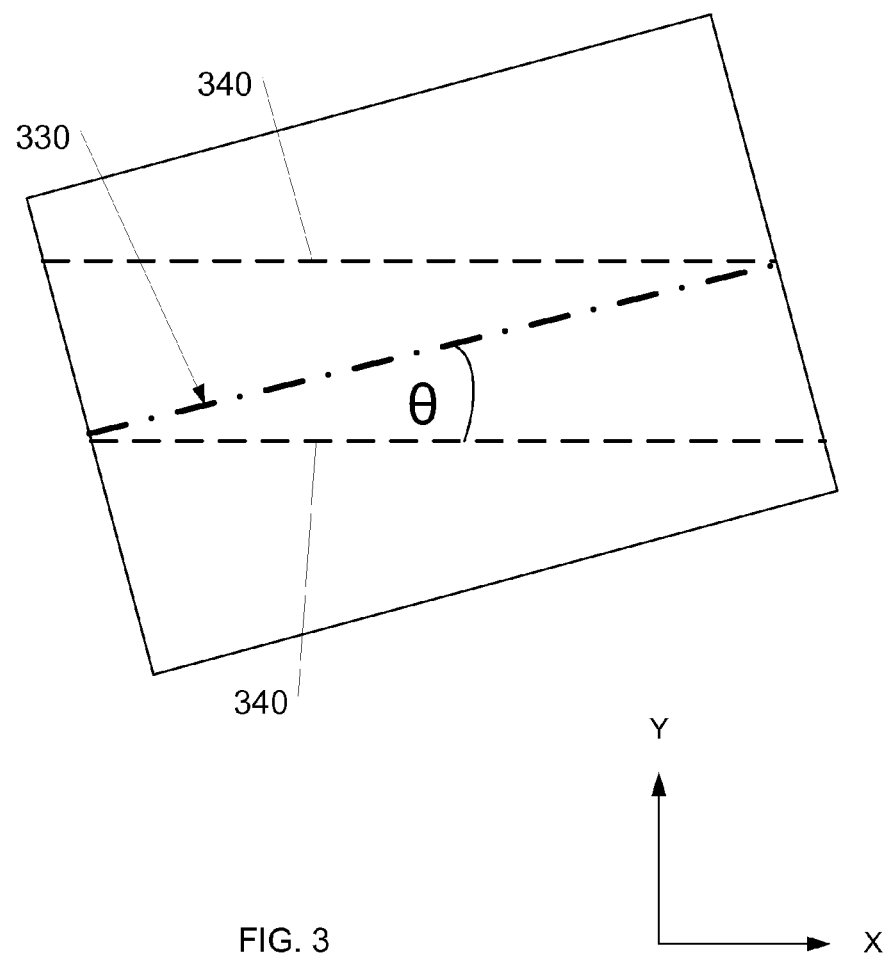
FIG. 3 is a top view of a microfluidic device having a quadrupole magnet array.

For example, FIG. 3 is a top view of a microfluidic device having a quadrupole magnet array. The interface 330 between two magnets in the top array is designated by the dashed-dotted line. The walls of the microfluidic channel beneath the top array are indicated by the dashed lines 340. As shown in FIG. 3, the interface 330 is oriented at an oblique angle θ with respect to the parallel walls 340, and thus also with respect to the central longitudinal axis, of the microfluidic channel. Since the focus position in the magnetic flux gradient follows the interface between the magnets, the location of the focus position through the channel also is oriented at an oblique angle with respect to the central longitudinal axis. Magnetizable particles traveling within the channel will tend to follow the position of the local minimum from one side of the channel to the other. The angle θ between can be anywhere between, e.g., 0° to 30°, including, for example, about 0.25°, about 0.5°, about 1°, about 1.5°, about 2°, about 3°, about 4°, about 5°, about 10°, or about 15°, Referring again to FIG. 2B, the focus position 216 in the magnetic flux gradient is shown positioned within the center of the microfluidic channel such that magnetizable particles are deflected to the channel center. It is not necessary, however, that the focus position actually be located at the center of the channel 208. Instead, the focus position 216 can be arranged at different lateral positions along the width of the channel (i.e., along the y-axis in FIG. 2B). The lateral location of the focus position flux gradient 216 can be altered by adjusting the lateral position of the interface 230 between the magnets in each array. To inhibit plaque aggregation, the focus position 216 should be maintained at least some minimum distance from the microfluidic channel walls. For example, the focus position can be set at least 50 µm away from the channel wall, at least 75 µm away from the channel wall, at least 100 µm away from the channel wall, at least 150 µm away from the channel wall, at least 200 µm away from the channel wall, or at least 225 µm away from the channel wall.

Since the magnitude of the flux gradient gives rise to the deflection force, the focus position 216 can, in some implementations, be located outside of the microfluidic channel with the high gradient portion of the flux gradient profile occurring within the channel.

Figure 2D:
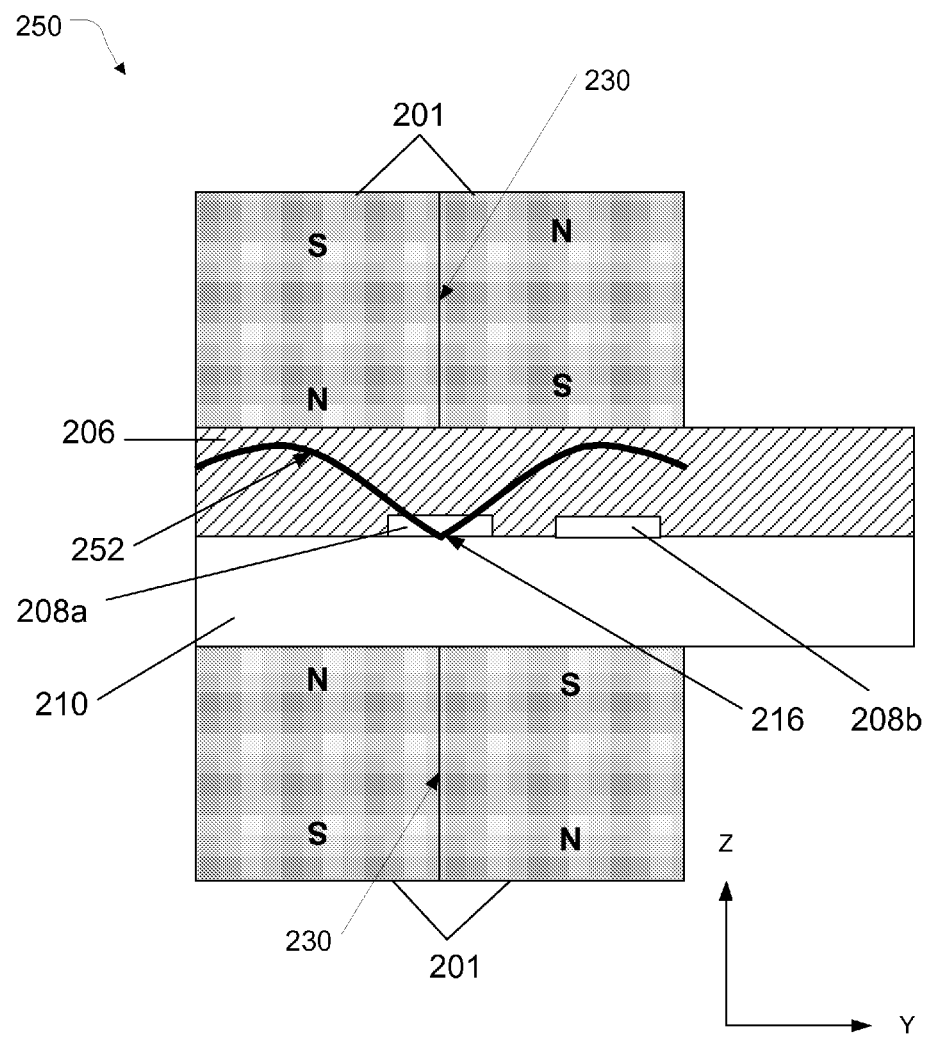
FIG. 2D is a schematic that illustrates a cross-section of a microfluidic device employing magnetophoresis that includes two microfluidic channels.

In some implementations, the flux gradient profile created by the magnet arrays extends through a second microfluidic channel. For example, FIG. 2D is a schematic that illustrates a cross-section of a microfluidic device 250 employing magnetophoresis that includes two microfluidic channels 208a, 208b. The two channels are separated by the microfluidic channel cover 206 and are on top of a glass substrate 210. An example of a flux gradient profile 252 generated by the magnet arrays is overlaid on the device to indicate the extent to which the flux gradient profile extends through both the first channel 208a and the second channel 208b. The focus position 216 that is bounded by the high gradient regions is located within the first channel 208a. One of the high gradient regions is located within the second channel 208b. Thus, magnetizable particles flowing through the second channel 208b experience a large deflection force relative to the force experienced by magnetizable particles flowing through the first channel 208a. The high flux gradient in the second channel 208b can therefore be used to deflect magnetizable particles having low magnetic moments. In contrast, the relatively low flux gradient in the first channel 208a can be used to deflect magnetizable particles having higher magnetic moments, since less magnetic force is needed to change the motion of those particles. In some implementations, the first and second channels 208a, 208b can be fluidly coupled together in series as a first isolation stage and a second isolation stage, respectively. The first stage then can be used to deflect the majority of magnetizable particles in the fluid sample, leaving a small fraction of magnetizable particles having low magnetic moment entering the second stage. The remaining magnetizable particles then can be deflected in the second stage due to the much higher magnetic flux gradient.

Figure 2E:
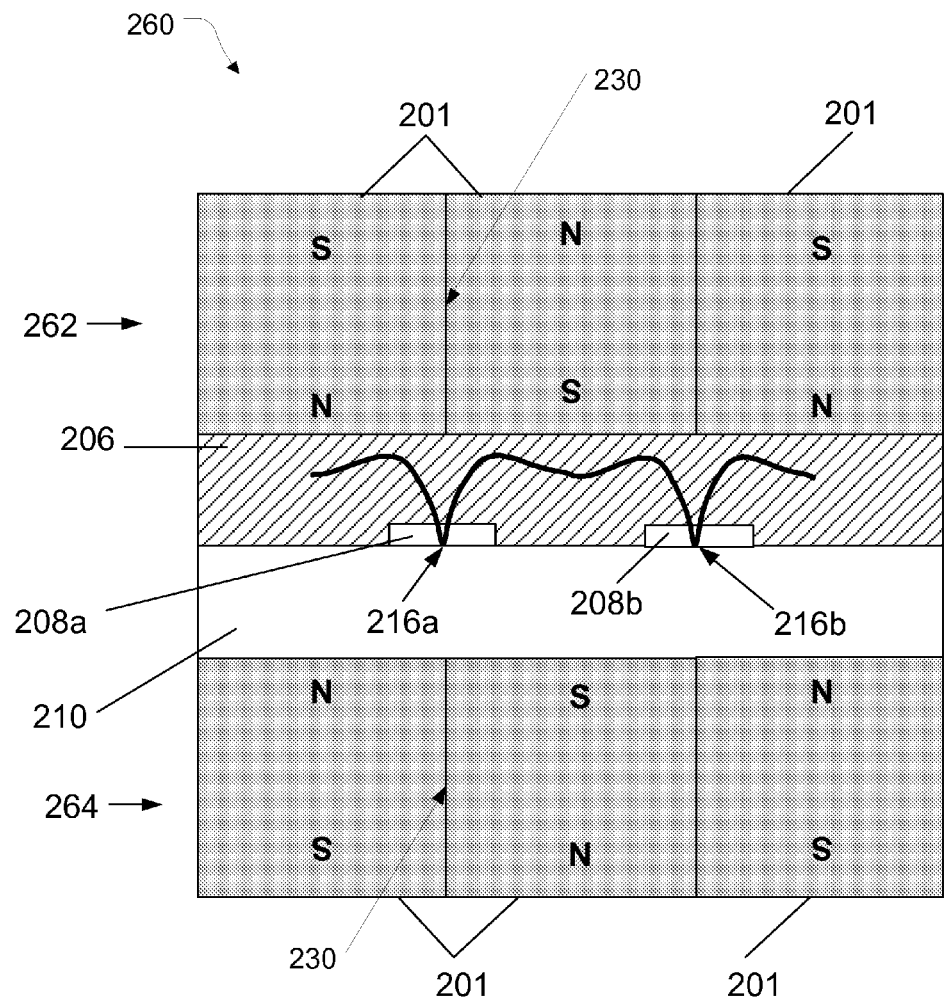
FIG. 2E is a schematic illustrating a cross-section of a microfluidic device that includes a first array of three magnets arranged above a microfluidic cover and a second array of three magnets arranged opposite the first array on a bottom of a substrate.

In some implementations, the magnet arrays in the magnetophoresis device include more than two magnets. If the arrays are arranged symmetrically with respect to one another (e.g., the interface between each pair of magnets in an array is aligned with a corresponding interface in the other array), it is possible to produce multiple focus regions, i.e., positions corresponding to a local minimum in the magnetic flux gradient that are bounded by local maxima in the magnetic flux gradient. The different focus regions can be aligned with different fluidic channels. By increasing the number of fluidic channels used for magnetophoresis, the amount of fluid sample that is processed can be increased, leading to an increase in the isolation/separation throughput. For example, FIG. 2E is a schematic illustrating a cross-section of a microfluidic device 260 that includes a first array 262 of three magnets 201 arranged on a top of a cover 206 and a second array 264 of three magnets 201 arranged on the bottom of a substrate 210. Each magnet 201 within the first array 262 is aligned to a corresponding magnet 201 in the second array 264 to produce two focus regions. A plot of the magnetic flux gradient profile overlaid on the device includes a first focus region 216a centered within a first channel 208a and a second focus region 216b centered within the second channel 208b. The plots overlaid on the device cross-sections in FIGS. 2D and 2E are approximations and may not correspond exactly to magnetic flux gradient profiles obtainable with the device arrangements shown. For example, in some implementations, the magnetic flux gradient between channel 208a and channel 208b in FIG. 2E may reach 0 T/m or close to 0 T/m.

Inertial Focusing

Though the magnetophoresis technique described herein can be used to deflect the trajectory of magnetizable particles in a fluid sample, the presence of other non-magnetizable particles distributed throughout the fluid sample may make efficient separation and collection of desired analytes difficult. To improve the separation and isolation achievable using magnetic deflection, both the magnetizable particles and the non-magnetizable particles can be aligned prior to entering the magnetophoresis region, such that their lateral positions within the channel are restricted and overlapping, e.g., following a single streamline. By ordering the analytes (magnetizable and non-magnetizable particles) within the fluid sample to the same streamline, the strong magnetic force in the magnetophoresis region then can be used to achieve highly sensitive separation of the magnetizable particles from the streamline, while leaving the non-magnetizable particles unaffected. As a result, one or more separate and distinct analyte streamlines can be formed for more efficient separation and collection.

An example of a technique for aligning both magnetizable and non-magnetizable particles prior to entering the magnetophoresis region is referred to herein as "inertial focusing." Inertial focusing uses inertial forces to enable the precise lateral positioning of particles within a microfluidic channel, e.g., along a common streamline. Inertial focusing is based upon the notion that laminar flow of a fluid through microfluidic channels can result in the continuous and accurate self-ordering of particles suspended within the fluid from a randomly distributed state.

For example, FIG. 1 illustrates an example of an inertial focusing region 104, in which the inertial focusing region is configured to localize fluid particles within a common streamline. The common streamline of particles enters the magnetophoresis region 102 at about the center of the microfluidic channel, where the magnetic flux gradient in region 102 subsequently deflects magnetizable particles from the common streamline, allowing separate isolation and collection of the magnetizable particles and the non-magnetizable particles.

In general, sorting, ordering, and focusing of particles in an inertial focusing system depends, inter alia, on the geometry of the microfluidic channel, the ratio of particle size to hydrodynamic cross-sectional size of the channel, and the speed of the fluid flow. Various channel geometries may require a predetermined particle-to-volume ratio of the particle to be focused to achieve a desired inter-particle spacing and thereby maintain ordering and focusing of those particles. In particular, the particle-to-volume ratio of a group of particles suspended within a fluid can be calculated and adjusted as needed to achieve focusing within certain channel geometries. In general, a maximum particle-to-volume ratio for a specified particle size and channel geometry can be determined using the formula:

$$MaxVolumeFraction = \frac{2N\pi a^2}{3hw}$$

where N is the number of focusing positions in a channel, a is the focused particle diameter, h is the microfluidic channel height, and w is the channel width.

Different microfluidic channel geometries can be used to achieve inertial focusing of particles. For example, the microfluidic channel can be a symmetrically curved channel, such as S-shaped, sinusoidal, or sigmoidal. The channel can have various cross-sections, such as a rectangular, elliptical, or circular cross-section. Alternatively, the channel can be an asymmetrically curved channel having various shapes, cross-sections, and configurations as needed for a particular application. For example, similar to the inertial focusing region 104 shown in FIG. 1, the channel can generally have the shape of a wave having large and small turns, where a radius of curvature can change after each inflection point of the wave. The maximum particle-to-volume ratio can be adjusted as necessary for the particular geometry.

The channel can be configured to focus particles within a fluid sample into one or more discrete streamlines at one or more equilibrium positions within the channel. In general, separation, ordering, and focusing are primarily controlled by a ratio of particle size to channel size and the flow characteristics of the system, but is independent of particle density. For example, analytes can have a hydrodynamic size that is in the range of about 1000 microns to about 0.01 microns. More particularly, analytes can have a hydrodynamic size that is in the range of about 500 microns to about 0.1 micron, such as between about 100 microns and about 1 micron. In general, the analyte size is limited by channel geometry. Analytes that are both larger and smaller than the above-described ranges can be ordered and focused within inertial focusing regions having laminar flow conditions.

Lateral migration of particles in shear flow arises from the presence of inertial lift, which is attributed mainly to the shear-gradient-induced inertia (lift in an unbounded parabolic flow) that is directed down the shear gradient toward the wall, and the wall induced inertia which pushes particles away from the wall. Particles suspended in fluids are subjected to drag and lift forces that scale independently with the fluid dynamic parameters of the system. Two dimensionless Reynolds numbers can be defined to describe the flow of particles in closed channel systems: the channel Reynolds number ($R_c$), which describes the unperturbed channel flow, and the particle Reynolds number ($R_p$), which includes parameters describing both the particle and the channel through which it is translating:

$$R_c = \frac{U_m D_h}{v}$$

and $$R_p = R_c \frac{a^2}{D_h^2} = \frac{U_m a^2}{v D_h}.$$

Both dimensionless groups depend on the maximum channel velocity, $U_m$, the kinematic viscosity of the fluid, and $v=\mu/\rho$ ($\mu$ and $\rho$ being the dynamic viscosity and density of the fluid, respectively), and $D_h$, the hydraulic diameter, defined as $2wh/(w+h)$ (w and h being the width and height of the channel, respectively, for a channel having a rectangular or square cross-section). The particle Reynolds number has an additional dependence on the particle diameter a. The definition of Reynolds number based on the mean channel velocity can be related to $R_c$ by $R_e=2/3R_c$. Inertial lift forces dominate particle behavior when the particle Reynolds number is of order 1. Typically, particle flow in microscale channels is dominated by viscous interactions with $R_p \ll 1$. In these systems, particles are accelerated to the local fluid velocity because of viscous drag of the fluid over the particle surface. Dilute suspensions of neutrally buoyant particles are not observed to migrate across streamlines, resulting in the same distribution seen at the inlet, along the length, and at the outlet of a channel. As $R_p$ increases, migration across streamlines occurs in macro scale systems. An example of $R_p$ that allows localization of a flux of cells from a blood sample within a rectangular or square channel is about 2.9, but this can range from about 0.02 to 2.9 or higher. Again, different microfluidic channel geometries can be used to achieve inertial focusing of particles, resulting in corresponding Reynolds numbers suitable for those channel geometries. Examples and further discussion of inertial focusing can be found, for example, in U.S. Pat. No. 8,186,913, which is incorporated herein by reference in its entirety.

As explained above, inertial focusing enables the precise lateral positioning of particles within a microfluidic channel. Positioning both magnetizable and non-magnetizable particles to the same position allows highly sensitive separation of the two populations using magnetophoresis. The particles that are not deflected by the magnetic force in the magnetophoresis region continue to follow the initial streamline on which they were located after leaving the inertial focusing stage. Inertial focusing can be important in certain implementations, such as the capture yield of circulating tumor cells (CTCs). A shift in the focus position or the focus quality of the inertially focused stream, defined by the full-width-half-maximum (FWHM) of the cell distribution along the cross-section of the flow channel, may result in a reduction in the cell capture yield when combined with magnetophoresis. Preferably, the focused stream is positioned to within a safety margin of +/-10%, e.g., within +/-5, 6, 7, 8, or 9%, around the position of the local minimum in the absolute value of the magnetic flux gradient.

In addition to enabling efficient separation and collection of desired targets from a fluid sample, the combination of inertial focusing and magnetophoresis also can be used to improve collection throughput. For instance, in certain implementations, it is desirable to increase the residence time that a magnetizable particle spends in the magnetophoresis region. Specifically, increasing the residence time results in a longer deflection distance for the magnetizable particles, and thereby increases the efficacy of particle separation. However, an increase in residence time also requires reduced flow rates for a fixed channel distance, which in turn results in a reduced rate at which desired particles are separated from undesired particles. To increase the separation throughput for a single channel having a fixed length, multiple inertially focused streams can be introduced into the channel. Various different implementations of a microfluidic system that combine inertial focusing with magnetophoresis (e.g., as separate devices or in a single device) are possible.

Single Stage Devices

Figure 4:
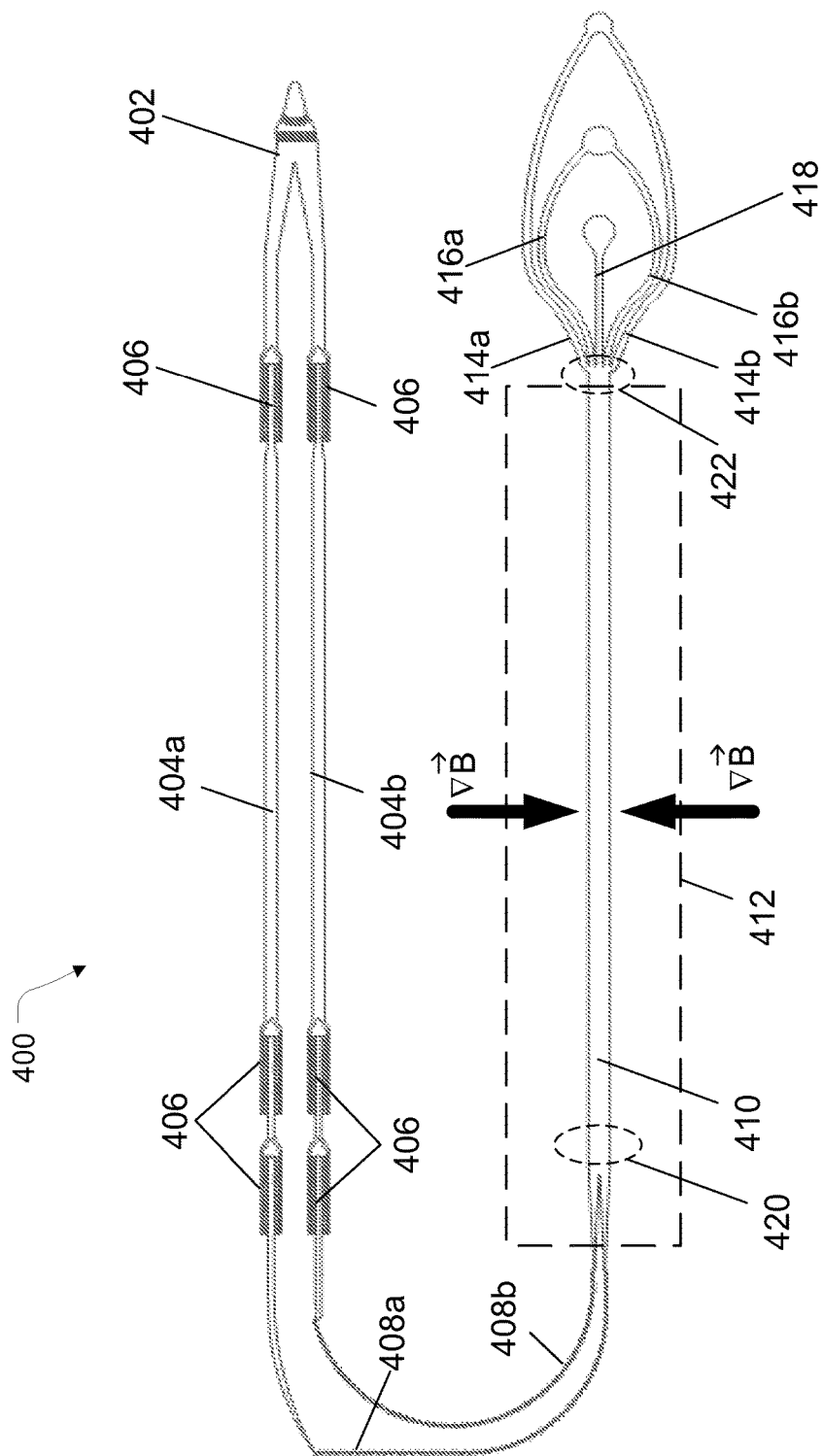
FIG. 4 is a schematic top view of a system that combines a region configured to induce inertial focusing and a region for isolation of analytes based on deflection by magnetic flux gradients.

For example, FIG. 4 is a schematic top view of a system 400 that combines a region configured to induce inertial focusing and a region for isolation of analytes based on deflection by magnetic flux gradients. For ease of viewing, only the outlines of the fluidic channels are shown. The inertial focusing portion and the magnetophoresis portion of the system can be formed in a single integral device, but they also can be formed separately and connected to be in fluid communication. A fluid sample containing both non-magnetizable analytes and analytes bound to magnetic particles enters the system 400 at input port 402. The fluid sample can be provided using, for example, a syringe pump. The fluid sample then is separated evenly into two parallel channels 404a, 404b. Each channel may optionally include one or more inlet filters 406 to remove or break up large debris in the fluid sample. For example, in the case of a fluid sample containing a mixture of leukocytes bound to magnetic particles and CTCs, the inlet filters 406 can be used to break up existing aggregates of the cells in the sample. A filter can include, for example, many narrow (~30 µm) channels arranged in parallel. Particles, e.g., cells, small enough to pass through the filters should also be small enough to pass through the larger structures downstream. The analytes in the fluid sample then enter inertial focusing regions 408a, 408b.

In the example shown in FIG. 4, the inertial focusing regions are channels having the shape of a wave with large and small turns, although other designs may be used. The analytes within each inertial focusing region then are focused to a corresponding common streamline (i.e., one common streamline from each channel). Each common streamline then flows into a single channel 410 in a magnetophoresis region designated by dashed line 412. The magnetophoresis region 412 can be configured, as described above, to deflect magnetizable particles within each flow stream using magnetic flux gradients.

Several exit channels are located at the output of the channel 410 for collecting waste particles, any desired analytes, and buffer solution. For instance, in the example shown in FIG. 4, the magnetophoresis channel 410 is fluidly coupled to two different outer channels 414a, 414b for receiving buffer fluid, two different inner channels 416a, 416b for receiving analytes in the sample fluid that are not bound to magnetic particles, and a central channel 418 for receiving analyte that are bound to magnetic particles. During operation of the device 400, the magnetic flux gradient, $\vec{\nabla}\vec{B}$, extends across the channel 410 and has a shape similar to the profile shown in FIG. 2B. If the local minimum in the magnetic flux gradient is located near the center of the channel 410, as measured in the y-direction (and the maxima that bound the local minimum are of opposite sign), the direction of the resulting force is toward the channel center. Accordingly, particles from each streamline will be deflected particles toward the channel center and away from the channel walls. By deflecting the particles away from the channel walls, the formation of plaques can be avoided. The deflected particles then can be collected at the central channel 418. The remaining analytes in each focused streamline will continue to travel along their initial trajectory.

Figure 5B:
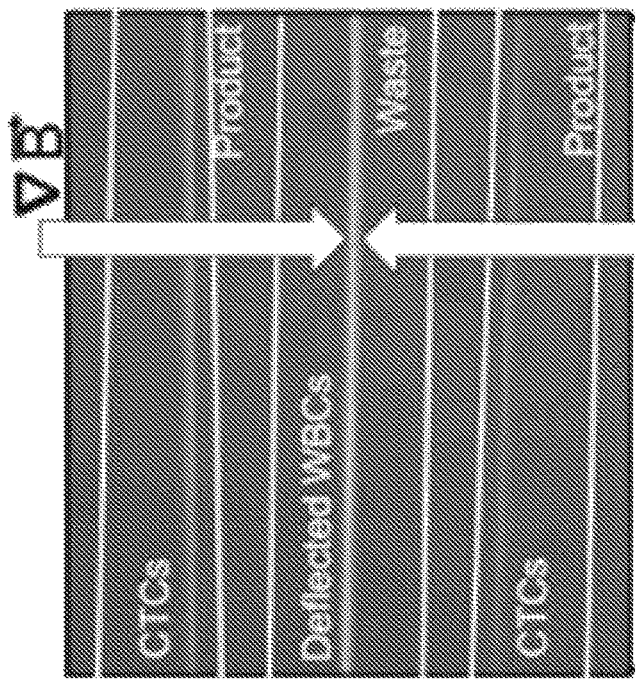
FIG. 5B is a schematic that shows separate inertially focused streamlines and a streamline of magnetically deflected particles exiting a magnetophoresis region of a microfluidic device.
Figure 5A:
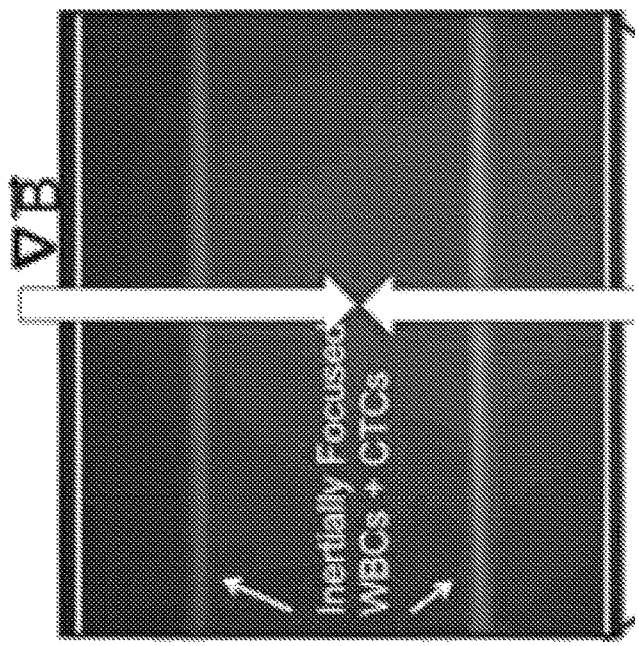
FIG. 5A is a schematic that shows separate inertially focused streamlines entering into a magnetophoresis region of a microfluidic device.

FIG. 5A is a schematic of what the separate inertially focused streamlines might look like upon entering the channel 410 at region 420 of the system 400. Each streamline shown in FIG. 5A includes, for example, white blood cells (WBCs) bound to magnetic particles and non-magnetizable CTCs. As the streamlines traverse the length of the channel 410 and are exposed to the magnetic flux gradient having the local minimum near the channel center, the deflected white blood cells are focused to a new streamline in the channel center. FIG. 5B is a schematic that shows the output of channel 410 at region 422 after the magnetizable particles have been deflected. As can be seen in FIG. 5B, the deflected WBCs have substantially separated from the inertially focused streams and are flowing into the central channel 418 (labeled "waste" in FIG. 5B). In contrast, the remaining particles in the inertially focused streams that were not deflected propagate into the inner channels 416a, 416b (labeled "product" in FIG. 5B). It should be noted that although the central and inner channels are labeled "waste" and "product," respectively, there is no limitation on the intended use of the output channels. For example, the magnetizable particles entering central channel 418 can include product that one desires to isolate and further analyze, whereas the analytes entering inner channels 416a, 416b from the inertially focused streams can include waste material. Both the deflected particles and the non-deflected particles may be collected at the respective outputs of the channels 416 and 418.

Multi-Stage Devices

As explained above, magnetophoresis can be implemented in a two-stage design, where a portion of analytes bound to magnetic particles in a fluid sample are deflected in a first stage, and second portion of analytes bound to magnetic particles are deflected in a second stage. In some implementations, the two-stage design also can be fluidly coupled to one or more inertial focusing stages (e.g., as part of the same device or a separate device), to provide inertially focused streamlines to the first stage and to the second stage.

Figure 6:
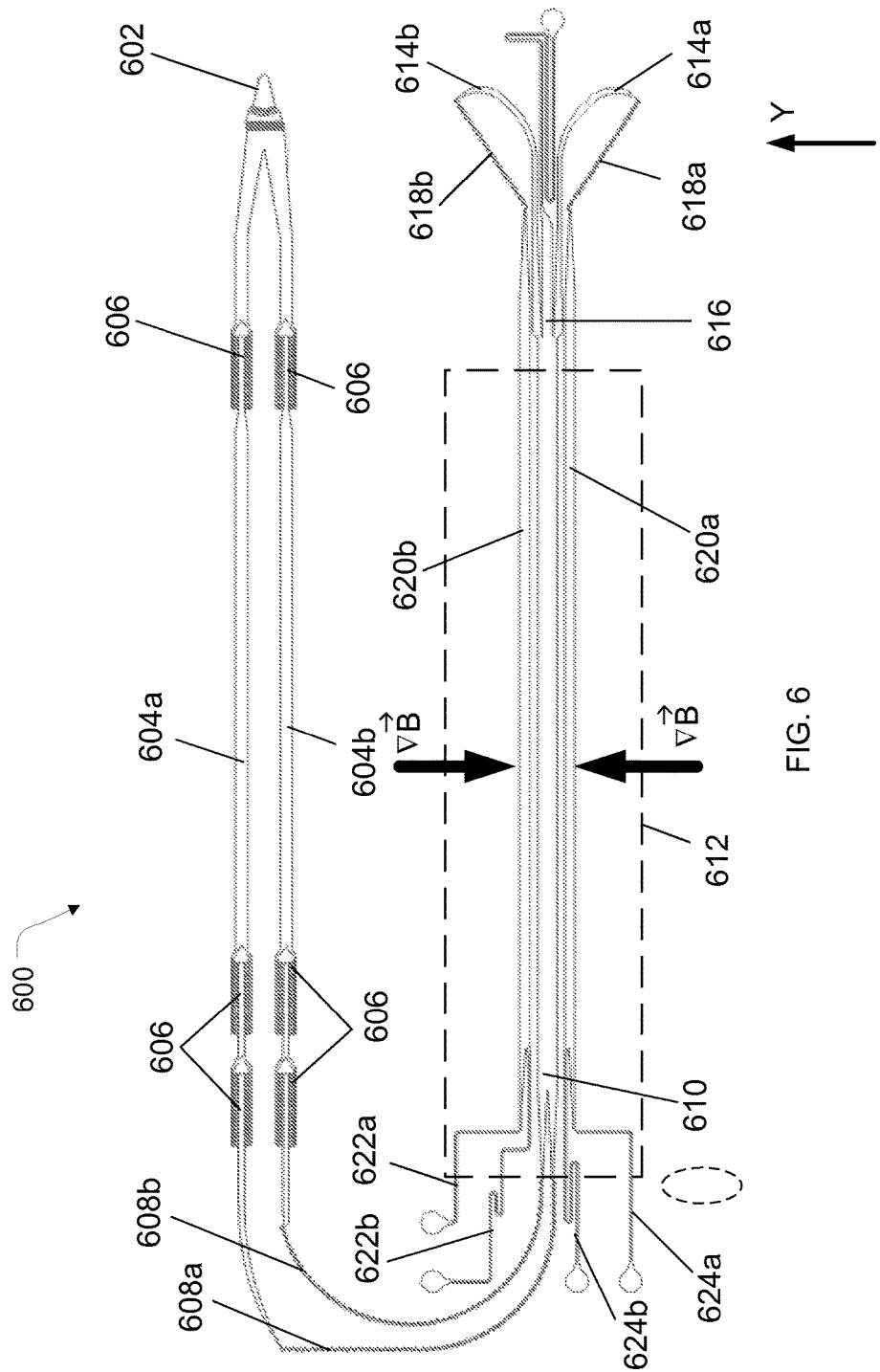
FIG. 6 is a schematic top view of a system that combines a region configured to induce inertial focusing and a region for isolating analytes based on deflection by magnetic flux gradients.

As an example, FIG. 6 is a schematic top view of a system 600 that combines a region configured to induce inertial focusing and a region for isolating analytes based on deflection by magnetic flux gradients. For ease of viewing, only the outlines of the fluidic channels are shown. It is assumed that the inertial focusing portion and the magnetophoresis portions of the system are formed in a single integral device. A fluid sample containing both non-magnetizable analytes and analytes bound to magnetic particles enters the system 600 at input port 602. The fluid sample can be provided using, for example, a syringe pump. Similar to the operation of the system shown in the example of FIG. 4, the fluid sample is separated evenly into two parallel channels 604a, 604b. Each channel may optionally include one or more inlet filters 606 to remove or break up large debris in the fluid sample. For example, in the case of a fluid sample containing a mixture of leukocytes bound to magnetic particles and CTCs, the inlet filters 606 can be used to break up existing aggregates of the cells in the sample.

The filters can include, for example, arrays of elongated posts, in which the fluid sample is forced to flow through open areas between posts. The analytes in the fluid sample then enter inertial focusing regions 608a, 608b. Again, the inertial focusing regions are channels having the shape of a wave with large and small turns, although other configurations are possible. The analytes within each inertial focusing region then are focused to a corresponding common streamline (i.e., one common streamline from each channel). Each common streamline then flows into a single channel 610 in a magnetophoresis region designated by dashed line 612. The magnetophoresis region 612 can be configured, as described above, to deflect magnetizable particles within each flow stream using a magnetic flux gradient.

If the local minimum in the flux gradient is located at the center of the channel as measured along the y-axis (and the maxima that bound the local minimum have opposite signs), a large portion of the magnetizable particles may be deflected toward the channel center. Several exit channels are located at the output of the channel 610 for collecting the deflected particles as well as the remaining inertially focused streams. For example, the magnetophoresis channel 610 is fluidly coupled to a center channel 616 for receiving particles that have been deflected using the magnetic flux gradient. The deflected particles then may be collected at an output of the center channel 616. The magnetophoresis channel 610 also is fluidly couple to two different outer channels 614a, 614b for receiving analytes remaining in the inertially focused streams.

The analytes collected by channels 614a, 614b are redirected to second inertial focusing stages 618a, 618b. In the present example, the second inertial focusing stages 618a, 618b are configured to have a shape of a wave with large and small turns, although other configurations are possible. The second inertial focusing stages 618a, 618b focus the remaining analytes in each of their respective channels into common streamlines that are introduced into microfluidic channels 620a, 620b associated with the second stage of the magnetophoresis device. The system 600 is configured such that the magnetic flux profile extends into channels 620a, 620b. Thus, the remaining magnetizable particles within the focused streamlines experience a deflection force which can separate those particles from the streamlines. The direction of the applied force depends on the sign of the magnetic flux gradient. In the example shown in FIG. 6, magnetizable particles have a magnetic moment in channel 620a will experience a force in the positive y-direction, whereas magnetizable particles in channel 620b will experience a force in the negative y-direction.

Multi-stage magnetophoresis systems, such as the two-stage system 600, enable a high-dynamic range for isolating different analytes. For example, the first stage can capture analytes that may have a large magnetic moment and that would otherwise be trapped in the second stage. The large magnetic moment may be due to a large number of magnetic particles bound to the analytes in a fluid sample or because the magnetic particles in the fluid sample each have a high magnetic moment. The second stage is more sensitive and thus can capture analytes that have a smaller magnetic moment. For example, the analytes captured in the second stage may be bound to a second type of magnetic particles, each of which has a lower magnetic moment relative to a first type of magnetic particle, or the analytes captured in the second stage may be bound to fewer magnetic particles than the analytes captured in the first stage. For example, if the analytes are cells, the first stage can capture cells that express a specific surface marker molecule at a high level (so that many magnetic particles are bound to the many surface markers), while the second stage can capture cells that express the same surface marker, but at a lower level (so that fewer magnetic particles are bound to the surface of these cells).

Figures 7A, 7B:
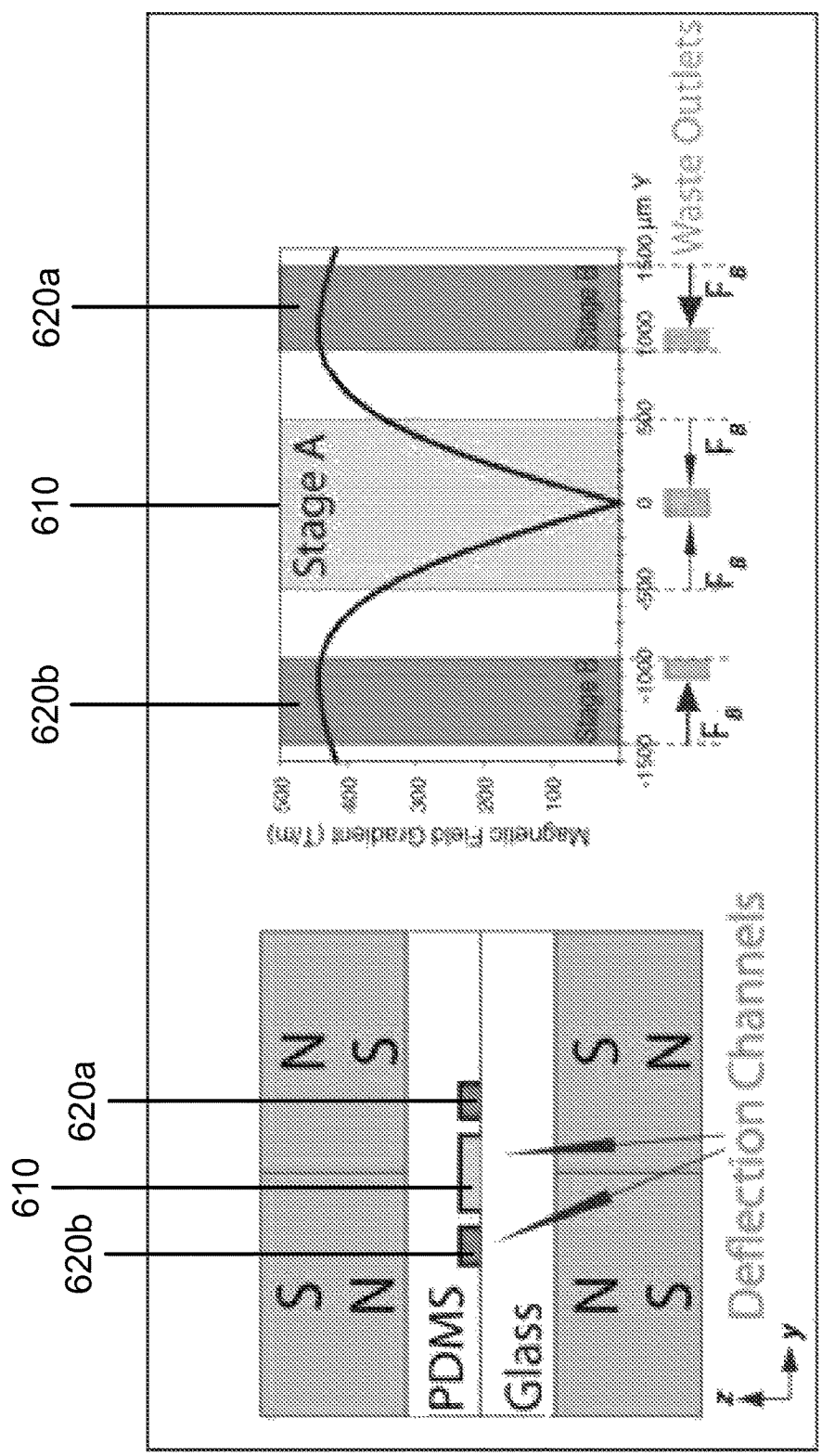
FIG. 7A is a schematic that illustrates a cross-section view of a magnetophoresis device having two deflection stages.
FIG. 7B is a plot of the magnetic gradient flux profile versus lateral distance for the device shown in FIG. 7A.

When the second stage of the system 600 is intended to isolate particles expressing a low magnetic moment using the same magnetic flux gradient, it is desirable to align the second stage microfluidic channels 620a, 620b with the location of the maximum magnetic flux gradient. Depending on the shape of the magnetic flux gradient profile, the deflection channels 620a, 620b in the second stage of the magnetophoresis portion of the system may need to be arranged close to the deflection channel 610 in the first stage. FIG. 7A is a schematic that illustrates a cross-section view of a magnetophoresis device having two deflection stages, similar to FIG. 6 (i.e., a first stage microfluidic channel 610 and two second stage microfluidic channels 620a, 620b). FIG. 7B is a plot of the magnetic gradient flux profile versus lateral distance for the device shown in FIG. 7A, in which the regions corresponding to the different microfluidic channels in the magnetophoresis device are shaded. As shown in FIG. 7B, the second stage fluidic channels 620a and 620b are arranged at about 500 μm away from the first stage fluidic channel 610 so that the maxima in the flux gradient are located at positions in or near the second stage fluidic channels 620a, 620b. Due to the higher gradient in the second stage channels, the deflection of magnetic particles can be maximized. The arrows beneath the plot of FIG. 7B indicate the direction of force in each of the channels. The shaded regions next to the arrows indicate the region of the channel where deflected particles will accumulate in response to the magnetic forces.

Referring again to FIG. 6, once the magnetizable particles have been deflected, the fluid sample in each second stage magnetophoresis channel reaches output channels 622a, 622b, 624a, 624b. For the flux gradient profile shown in FIG. 7B, deflected particles in channels 620a, 620b will flow into output channels 622b and 624b, respectively. Any remaining fluid sample including non-deflected particles in channels 620a, 620b will flow into output channels 622a, 624a, respectively.

Figure 8:
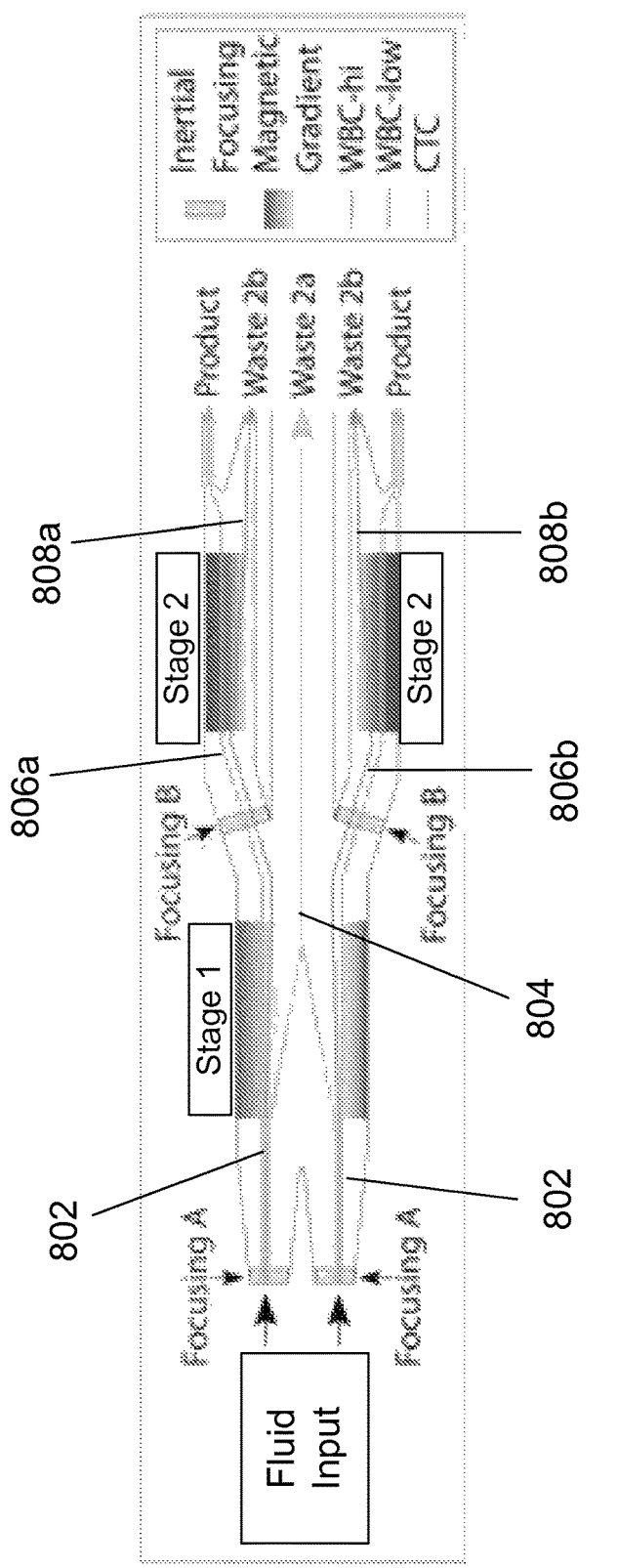
FIG. 8 is a schematic that generalizes the isolation process of magnetizable and non-magnetizable particles in a two-stage magnetophoresis system.

FIG. 8 is a schematic that generalizes the isolation process of magnetizable and non-magnetizable particles in a two-stage magnetophoresis system such as the system 600 shown in FIG. 6. The fluid sample is assumed to include CTCs that are not bound to any magnetic particles and WBCs that are bound to magnetic particles. Some of the magnetically labeled WBCs express a high magnetic moment, whereas some of the magnetically labeled WBCs express a low magnetic moment. As shown in FIG. 8, the fluid sample is introduced into two separate inertial focusing regions (labeled "Focusing A") simultaneously. The inertial focusing regions focus the CTCs and WBCs into separate streamlines 802a, 802b. The focused streamlines then enter a common microfluidic channel in a first magnetophoresis region (labeled "Stage 1"). In Stage 1, the magnetic flux gradient deflects WBCs expressing a high magnetic moment to a focus position 804. The deflected WBCs proceed to travel along the focus position to a waste channel (labeled "Waste 2a"). The remaining analyte streamlines each pass through a second corresponding inertial focusing region (labeled "Focusing B"), where the analytes are re-focused to new lateral positions 806a, 806b. The newly focused streamlines then enter microfluidic channels in a second magnetophoresis region (labeled "Stage 2"). In Stage 2, the streamlines from the inertial focusing region are aligned at or near the maxima in magnetic flux gradient. The flux gradient deflects the WBCs expressing a low magnetic moment to new focus positions 808a, 808b. The deflected WBCs follow the new focus positions to waste channels (labeled "Waste 2b"). In contrast, the now isolated CTCs propagate into collection channels (labeled "Product").

As with the single stage device, the two-stage device also allows an increase in magnetically labeled particle residence time in the magnetophoresis region, while maintaining high throughput. The multistage device also helps reduce clogging by removing in the first stage magnetic particle aggregates that, as a result of the large number of magnetic particles, may express a high magnetic moment. With the reduction in clogging, the multi-stage device enables, in some implementations, the use of larger magnetic particles and higher magnetic particle concentrations. Additionally, the use of the two-stage design enables, in some implementations, substantially higher depletion of the magnetically labeled particles from a fluid sample. For example, the two-stage system can enable depletion of magnetically labeled particles from a fluid sample of greater than or equal to about 95%, greater than or equal to about 97%, greater than or equal to about 99%, greater than or equal to about 99.9%, and greater than or equal to about 99.99% (about 4 log depletion of unwanted analytes).

Hydrodynamic Sorting

When handling certain fluids, such as whole blood, it can be useful to first separate a large number of unnecessary constituents that may otherwise reduce the isolation efficiency of the magnetophoresis region. For example, as shown in FIG. 1, an optional hydrodynamic sorting region 106 may be used to separate out non-nucleated cells (e.g., platelets and/or red blood cells) from whole blood prior to introducing the fluid sample into the first inertial focusing region of either the single-stage or two-stage microfluidic systems described herein.

The hydrodynamic sorting region can be based on a technique known as deterministic lateral displacement (DLD). For example, in some implementations, DLD employs an array of posts having a pillar size and array offset designed to deflect particles above a certain size, thereby separating them from the main fluid suspension. A key parameter for DLD arrays is the critical deflection diameter ($D_c$), which is the minimum particle hydrodynamic diameter deflected by the DLD array. More specifically, particles whose hydrodynamic diameter is smaller than the array's $D_c$ are not deflected by the presence of the pillar array, and follow the primary fluid streamlines around the posts. Conversely, particles whose hydrodynamic diameter is larger than $D_c$ are deflected by the array. The critical deflection diameter depends, in part, on three array parameters: row shift fraction ($\varepsilon$), horizontal gap between adjacent pillars ($g_H$), and the array geometrical factor ($\eta$). A mathematical expression for $D_c$ can then be written as:

$$D_c = 2\eta g_H \varepsilon$$

The array geometrical factor $\eta$ accounts for non-uniform flow through the horizontal gap between adjacent pillars, and depends on array arrangement, pillar shape, as well as material and surface properties. Determination of $\eta$ requires one to resolve the flow profile within the gap ($u(x)$), from which the array geometrical factor can be computed as:

$$\int_0^\beta u(x)dx = \varepsilon \int_0^{g_h} u(x)dx$$

where $\beta = \eta g_H \varepsilon$. Numerical simulation tools (e.g., COMSOL or Ansys) can be used to model different array configurations and determine their associated $D_c$. In some implementations, analytical solutions may be available for certain array configurations where the flow profile is known a priori (e.g., array of cylindrical micropillars in a square arrangement). Further details on the design and fabrication of hydrodynamic sorting arrays can be found, for example, in U.S. Patent App. Publication No. 2006/0134599 and U.S. Patent No. 8,021,614, each of which is incorporated herein by reference in its entirety.

Figure 9B:
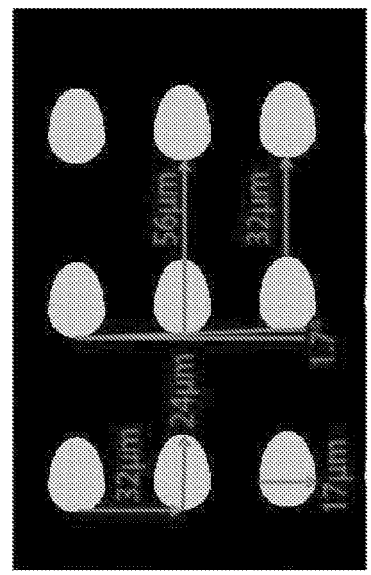
FIG. 9B is a schematic that illustrates the dimensions of an example of a post array for a hydrodynamic sorting region.
Figure 9A:
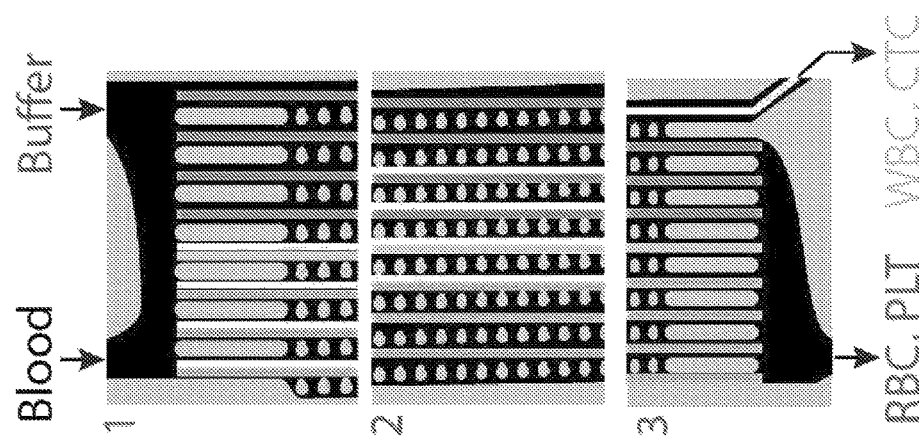
FIG. 9A is a schematic that depicts the flow of blood through a hydrodynamic sorting region containing an array of posts.

FIG. 9A is a schematic that depicts the flow of blood through one implementation of a hydrodynamic sorting region containing an array of posts. As shown in FIG. 9A, both blood and a buffer solution are provided into a first and second input, respectively. As the blood and buffer traverse the posts, the fluid sample constituents (e.g., red blood cells [RBCs] and platelets [PLTs]) below the array's critical dimension are sorted out of the fluid to the output on the left in the figure, whereas the fluid sample constituents above the critical diameter (e.g., WBCs and CTCs) are sorted out of the fluid to the output on the right in the figure. FIG. 9B is a schematic that illustrates the dimensions of an example post array for this particular hydrodynamic sorting region. As shown in FIG. 9B, the posts are "egg shaped," and are characterized by a 32 μm gap between adjacent posts, as well as a 1.7° slope between neighboring rows. The top surface of each post in this implementation has a maximum length of 24 µm and a minimum length of 17 µm. The period between adjacent posts is 56 µm. These array properties yield a 4 µm critical deflection diameter for the microarray. Note that other cross-sectional shapes can be used for the posts, such as circles, ovals, ellipses, rectangles, squares, triangles, hexagons, and octagons.

The hydrodynamic sorting region can be formed as a separate device that is fluidly coupled to the inertial focusing and magnetophoresis system (e.g., using multiple pumps and tubing) or as part of a single monolithic device. In some implementations, a hydrodynamic sorting region can be included upstream of the inertial focusing and magnetophoresis sections as well as down stream of the magnetophoresis section. By providing two separate hydrodynamic sorting regions, the depletion of non-desired particles (e.g., RBC or platelets when attempting to isolate CTCs) can be improved. For instance, the introduction of an additional hydrodynamic sorting region downstream of the magnetophoresis region may provide an additional 1-2 log depletion of RBCs or additional 1-3 log depletion of platelets compared to a system using only a single hydrodynamic sorting region upstream of the magnetophoresis region.

Fabrication of Microfluidic Devices

Figure 10:
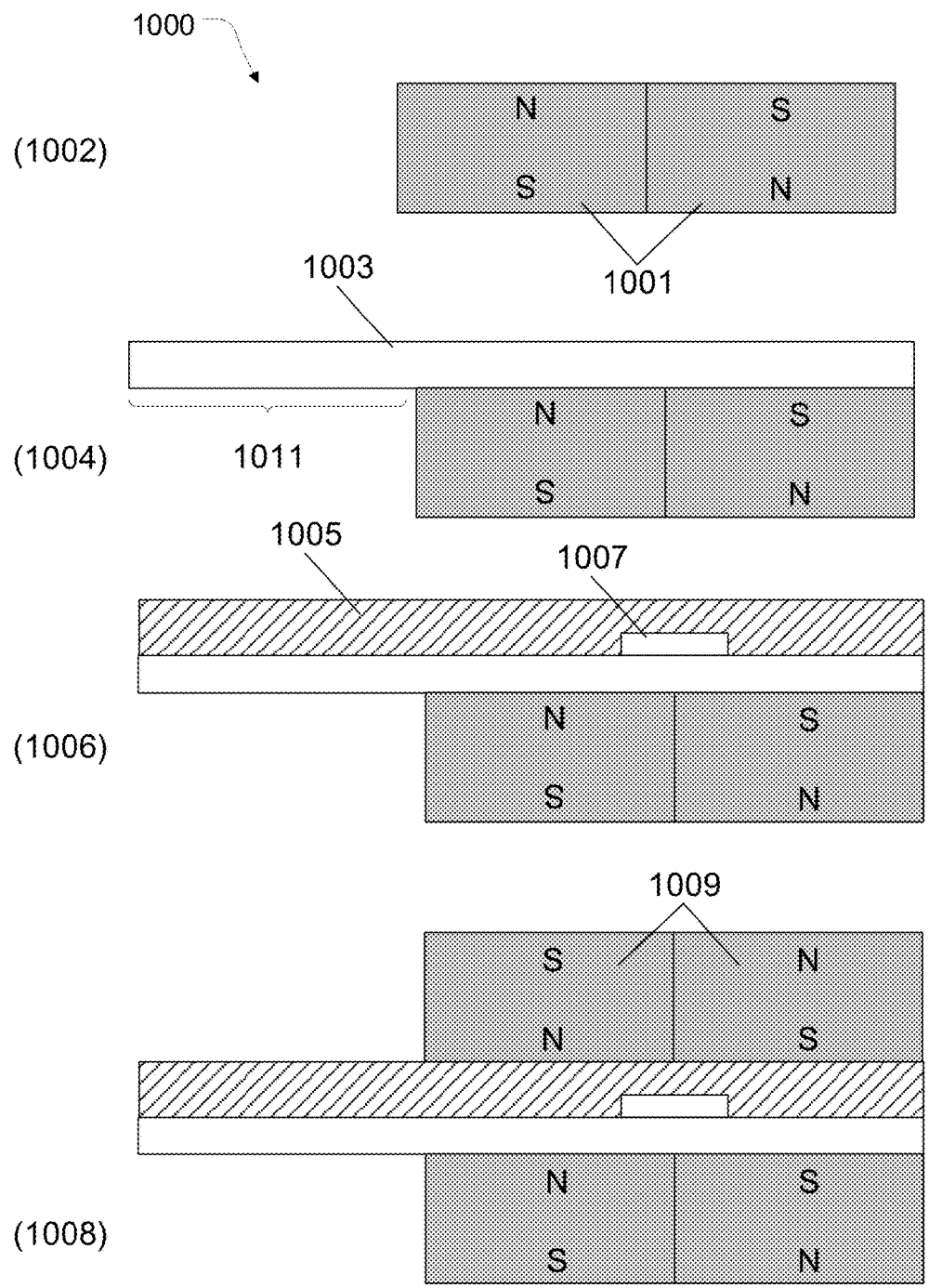
FIG. 10 is a schematic illustrating a process for fabricating a microfluidic device for isolating and/or separating target analytes using high magnetic flux gradients according to the present disclosure.

FIG. 10 is a schematic illustrating a process 1000 for fabricating a microfluidic device for isolating and/or separating target analytes using high magnetic flux gradients according to the present disclosure. Referring to FIG. 10, two or more magnets 1001 are initially provided (1002) to form a first array of magnets. The magnets 1001 can be made of any suitable magnetic material capable of emitting a high magnetic field (e.g., alloys of NdFeB, SmCo, AlNiCo, or ferrite) and are arranged such that each magnet has a polarization orientation that is the opposite of an adjacent magnet in the array. A substrate layer 1003 then is provided (1004) on a surface of the two or more magnets. The substrate layer can include any suitable low magnetic permeability material, e.g., a non-magnetic material, including, for example, glass, plastic or silicon wafer. An optional thin film layer (e.g., $SiO_2$) can be formed on a surface of the substrate layer using, for example, thermal or electron beam deposition, such that the thin-film is conserved a part of the magnetizable layer. In some implementations, the substrate layer 1003 can include a portion 1011 that extends beyond the width and length of the magnets. This portion 1011 can provide a base on which microfluidic regions other than the magnetophoresis region may be formed.

After providing the substrate layer, the microfluidic channel 1007 and cover 1005 are formed above the substrate layer (1006). In some implementations, the microfluidic channel and cover are formed by depositing a polymer (e.g., PDMS, PMMA or polycarbonate (PC)) in a mold that defines the fluidic channel regions. The polymer, once cured, then is transferred and bonded to a surface of the substrate layer. For example, PDMS can be first poured into a mold (e.g., an SU-8 mold fabricated with two step photolithography (MicroChem)) that defines the microfluidic network of channels. In addition, the portion 1011 of the cover extending beyond the magnets can be used to form the inertial focusing channels and filters that are fluidly coupled to the magnetophoresis region. The PDMS then is cured (e.g., heating at 65° C. for about 3 hours). Prior to transferring the solid PDMS structure to the device, the surface of the substrate layer is treated with $O_2$ plasma to enhance bonding. A second array of two or more magnets 1009 then is positioned (1008) on a surface of the cover. To secure the first and second array of magnets in place relative to the channel 1007, each array can be placed in a non-magnetic manifold, e.g., an aluminum manifold having a cavity/opening to receive the magnets. The magnets of each array may be secured in the corresponding manifold using an adhesive such as glue. The two manifolds then are secured together (using, for example, screws) with substrate and cover placed between them.

Careful alignment of the microfluidic channel to the magnetics can be important to the performance of the system, since focusing of magnetic particles occurs at position that is aligned with the interface between adjacent magnets in an array. Misalignment of the channel to the position corresponding to the local minimum in the absolute value of the magnetic flux gradient may result in magnetizable particles being deflected into the channel sidewalls. In addition to lateral alignment of the magnetic arrays to the channel, it is, in certain implementations, also important to properly align the channel to the magnetic array in the vertical direction (e.g., along the z-axis in FIG. 2A). The vertical alignment should be such that the center of the flow channel (as determined, for example, along the z-axis in FIG. 2A) is equidistant between the top and bottom magnets to establish a negligible gradient in the magnetic flux along the channel height.

Microfluidics

In some implementations, the microfluidic channel of the microfluidic devices described herein is part of a larger, optional, microfluidic channel network. Such microfluidic networks can be used to facilitate control and manipulation (e.g., separation, segregation) of small volumes of liquid and help isolate target analytes from a complex parent specimen. During the isolation process, microfluidic elements provide vital functions, for example, handling of biological fluids or reproducible mixing of magnetic particles with samples. Additional information about microfluidic channel networks and their fabrication can be found, for example, in U.S. Patent App. Publication No. 2011/0091987, U.S. Pat. Nos. 8,021,614, and 8,186,913, each of which is disclosed herein by reference in its entirety.

Use of Magnetic Particles

As noted above, a fluid sample that may contain a target analyte that is mixed with a liquid containing a number of particles that are designed to specifically bind to the target analyte. The particles can include magnetic particles (e.g., nanoparticles) that form a target-particle complex in solution.

Magnetic Particles

Magnetic particles can include one or more inner magnetic cores and an outer coating, e.g., a capping polymer. The magnetic cores can be monometallic (e.g., Fe, Ni, Co), bimetallic (e.g., FePt, SmCo, FePd, and FeAu) or can be made of ferrites (e.g., $Fe_2O_3$, $Fe_3O_4$, $MnFe_2O_4$, $NiFe_2O_4$, $CoFe_2O_4$). The magnetic particles can be nanometers or micrometers in size, and can be diamagnetic, ferromagnetic, paramagnetic, or superparamagnetic, in which size corresponds to an average diameter or average length. For example, the magnetic particles can have a size of approximately 1 µm, approximately 600 nm, approximately 500 nm, approximately 300 nm, approximately 280 nm, approximately 160 nm, or approximately 100 nm. Other particle sizes are possible as well. The outer coating of a particle can increase its water-solubility and stability and also can provide sites for further surface treatment with binding moieties. The magnetic particles each have a magnetic moment in the range of about 1 KA/m to about 100 kA/m. For example, in some implementations, the magnetic particles have a magnetic moment of about 35 kA/m Binding Moieties In general, a binding moiety is a molecule, synthetic or natural, that specifically binds or otherwise links to, e.g., covalently or non-covalently binds to or hybridizes with, a target molecule, or with another binding moiety (or, in certain embodiments, with an aggregation inducing molecule). For example, the binding moiety can be a synthetic oligonucleotide that hybridizes to a specific complementary nucleic acid target. The binding moiety can also be an antibody directed toward an antigen or any protein-protein interaction. Also, the binding moiety can be a polysaccharide that binds to a corresponding target. In certain embodiments, the binding moieties can be designed or selected to serve, when bound to another binding moiety, as substrates for a target molecule such as enzyme in solution. Binding moieties include, for example, oligonucleotides, polypeptides, antibodies, and polysaccharides. As an example, streptavidin has four sites (binding moieties) per molecule that will be recognized by biotin. For any given analyte, e.g., a specific type of cell having a specific surface marker, there are typically many binding moieties that are known to those of skill in the relevant fields.

For example, certain labeling methods and binding moiety techniques are discussed in detail in U.S. Pat. No. 6,540,896 entitled, "Microfabricated Cell Sorter for Chemical and Biological Materials" filed on May 21, 1999; U.S. Pat. No. 5,968,820 entitled, "Method for Magnetically Separating Cells into Fractionated Flow Streams" filed on Feb. 26, 1997; and U.S. Pat. No. 6,767,706 entitled, "Integrated Active Flux Microfluidic Devices and Methods" filed on Jun. 5, 2001.

Conjugate Preparation

The surface of the magnetic particles can be treated to present functional groups (e.g., $-NH_2$, $-COOH$, $-HS$, $-C_nH_{2n-2}$) that can be used as linkers to subsequently attach the magnetic particles to cells other target molecules (e.g., antibodies, drugs). In some cases, the surface treatment makes the magnetic particles essentially hydrophilic or hydrophobic. The surface treatment can include the use of polymers including, but not limited to, synthetic polymers such as polyethylene glycol or silane, natural polymers, derivatives of either synthetic or natural polymers, and combinations thereof.

In some implementations, the surface treatment does not result in a continuous film around the magnetic particle, but results in a "mesh" or "cloud" of extended polymer chains attached to and surrounding the magnetic particle. Exemplary polymers include, but are not limited to, polysaccharides and derivatives, such as dextran, pullanan, carboxydextran, carboxmethyl dextran, and/or reduced carboxymethyl dextran, PMMA polymers and polyvinyl alcohol polymers. In some implementations, these polymer coatings provide a surface to which targeting moieties and/or binding groups can bind much easier than to the particle. For example, in some embodiments magnetic particles (e.g., iron oxide nanoparticles) are covered with a layer of 10 kDa dextran and then cross-linked with epichlorohydrin to stabilize the coating and form cross-linked magnetic particles.

Additional information on the fabrication, modification, and use of magnetic particles can be found, for example, in PCT Pub. No. WO/2000/061191, U.S. Patent App. Pub. No. 20030124194, U.S. Patent App. Pub. No. 20030092029, and U.S. Patent App. Pub. No. 20060269965, each of which is incorporated herein by reference in its entirety.

Applications and Uses of the New Microfluidic Devices

The new microfluidic device described herein can be used in various applications including, for example, as part of a research platform to study analytes of interest (e.g., proteins, cells (such as CTCs in a patient's blood or fetal cells, e.g., in maternal blood), bacteria, pathogens, and DNA) or as part of a diagnostic assay for diagnosing potential disease states or infectious agents in a patient. Examples of detection targets are discussed in more detail below and in the Examples section.

Detecting Infectious Agents

By modifying the functional ligands (e.g., binding moieties) on the magnetic particles, the microfluidic devices described herein can be used to detect, isolate, and/or measure many different biological analytes, including small molecules, proteins, nucleic acids, pathogens, and cells, e.g., rare cells such as cancer cells.

Rare Cell Detection

The microfluidic devices and methods described herein can be used to detect and quantify rare cells, such as CTC in a blood sample, or fetal cells in blood samples of pregnant females. For example, primary tumor cells or CTCs can be targeted and specifically bound to magnetic particles and can be detected using the new microfluidic device for a rapid and comprehensive profiling of cancers. By changing binding molecules on the magnetic particle surface, different types of cells can be detected (e.g., circulating endothelial cells, e.g., as an indicator of heart disease). For example, instead of linking magnetic particles to CTCs, the magnetic particles can be specifically bound to white blood cells, which are then deflected using the magnetic flux gradients generated in the device. Thus, the microfluidic device may be used as a powerful diagnostic and prognostic tool.

The targeted and detected cells can be cancer cells, stem cells, immune cells, white blood cells (WBCs), or other cells including, for example, circulating endothelial cells (using an antibody to an epithelial cell surface marker, e.g., the Epithelial Cell Adhesion Molecule (EpCAM)), or circulating tumor cells (using an antibody to a cancer cell surface marker, e.g., the Melanoma Cell Adhesion molecule (CD146)). In some implementations, the system sensitivity can detect as low as a few cells or less per milliliter of detection volume, i.e., the device itself has the capacity for single-cell detection. An additional advantage of the system over a number of previous cell isolation techniques is that it enables detection and quantification of cells in suspension rather than requiring time-consuming immobilization on a chip. The combination of these factors enables high quality cytopathological evaluation of cells, single-cell RNA and genotyping analysis, and culture of CTCs. The systems and methods also can be used to detect small molecules, proteins, nucleic acids, or pathogens.

Multiplexed Detection

Detecting multiple biomarkers in one parent sample is an important and highly desirable task for diagnosis and prognosis of complex diseases. For example, there is no ubiquitous biomarker for cancer (examples of tumor cell biomarkers that can be detected include MUC-1, EGFR, B7-H3, Her2, Ki-67, EpCam, Vim, and CK18); multi-channeled screening is required to correctly identify different tumor types. The new microfluidic devices described herein offer methods to detect different relevant biomarkers from the aliquots of a single, parent sample, e.g., in patients with cancer or metabolic disorders. A multistage microfluidic device is well suited for this application. In a multistage device, different target analytes (e.g., white blood cell versus red blood cell) may be bound to different magnetic particles or different amounts of magnetic particles such that the different target analytes exhibit a different response to the flux gradient in the magnetophoresis region. The target analytes bound to magnetic particles having a high magnetic moment may be deflected easier than target analytes bound to magnetic particles having a lower magnetic moment.

Thus, in a first stage of the microfluidic device, the analytes expressing higher responsivity may be filtered out of the sample to isolate the analytes expressing the lower responsivity (or vice versa). In a second stage of the microfluidic device, the analytes expressing the lower responsivity to the flux gradient then can be filtered out from the sample.

In some implementations, different types of magnetic particles can be used to isolate different populations of cells. For example, a first population of cells within a fluid sample may be labeled with diamagnetic particles whereas a second population of cells within a fluid sample may be labeled with paramagnetic particles. Diamagnetic material has relative permeability<1, i.e., the absolute permeability is less than that of free space. Therefore, in a magnetic field, a diamagnetic material experiences a force oriented opposite to the force on a paramagnetic material. Thus, by using both paramagnetic and diamagnetic particles as magnetic labels for different cell populations, it is possible to use the magnetic flux gradient profile to separate a group of cells within a fluid sample into three separate streams: (1) those cells that are paramagnetic labeled, (2) those cells that are diamagnetic labeled, and (3) those cells that are unlabeled. For cells labeled with both diamagnetic and paramagnetic particles, such cells would, in certain implementations, follow the paramagnetic labeled stream, since the magnetic force on paramagnetic particles is generally several orders of magnitude larger than the magnetic force on diamagnetic particles.

In a particular example, paramagnetic beads labeled with CD45 and CD66b can bind to WBCs in a blood sample, whereas diamagnetic beads labeled with EpCAM and CDH11 can bind to CTCs. When the blood sample is passed through a magnetophoresis region having a magnetic flux gradient profile similar to the profiles described herein (see, e.g., FIG. 2B), the cells separate into (1) paramagnetic bead labeled WBCs, (2) unlabeled WBCs and CTCs, and (3) diamagnetic bead labeled CTCs. Effectively, this dual labeling approach is equivalent to simultaneous positive selection and negative selection of cells, thus allowing, in certain implementations, a highly pure collection of a desired target. For example, the cells labeled bound to the diamagnetic particles would not only be isolated during negative depletion from cells bound to CD45 and CD66b labeled paramagnetic beads, the diamagnetic bead bound cells would also experience a deflection away from the paramagnetic bead labeled cells.

As noted, CTCs can be isolated for early detection, monitoring, and/or diagnosis of cancer. However, CTCs are not the only cells that can be isolated using the devices and techniques described herein. Other cells, including, but not limited to, circulating epithelial cells (CECs), plasma cells, megakaryocytes, progenitor cells, nuclieoli, heme (producing) cells, or sub-sets of heme (producing) cells also can be isolated using positive or negative selection based on magnetic particle labeling and exposure to magnetic forces as described herein. For example, the desired cells can include CECs, plasma cells, megakaryocytes, progenitor cells, and/or nuclieoli that are isolated by depleting unwanted cell populations, such as heme cells, or sub-sets of heme cells that are bound to magnetic particles. In another example, the use of negative depletion based on magnetic flux gradients can be applied to isolate stem cells from peripheral blood and bone marrow.

In some implementations, the devices and techniques described herein can be used to prepare blood samples for transfusion. For example, CTCs and/or other cells may be isolated from healthy blood cells using negative depletion to remove the CTCs and other cells from the blood sample prior to transfusion. Positive and/or negative depletion according to the present disclosure may be used to isolate other cells such as: dendritic cells for analyzing immune response infections, and/or allergies; hematopoietic stem cells for performing stem cell therapy and/or regenerative medicine; endothelial progenitor cells for performing vascular regeneration, diagnosis, and/or transplantation; fibrocytes for assisting wound healing; antigen specific T cells for performing work on vaccine development, monitoring latent infection, and/or tuberculosis identification; and fetal cells for performing genetic testing and prenatal diagnosis.

EXAMPLES

The invention is further described in the following examples, which do not limit the scope of the invention described in the claims.

Example 1

Isolating Cancer Cells in Blood

The purpose of this example was to simulate a cancer patient's blood by spiking cell line cancer cells to represent circulating tumor cells (CTCs) into a healthy donor's blood sample, efficiently tagging white blood cells with magnetic beads, and removing the tagged white blood cells using magnetophoresis to isolate the cancer cells for detection and/or further measurements. The protocol below describes the isolation of CTCs using a system that employed continuous (i) deterministic lateral displacement (hydrodynamic cell sorting) for size-based separation of both white blood cells and tumor cells from whole blood, (ii) inertial focusing for precise positioning of these cells in a micro-channel, followed by (iii) microfluidic magnetophoresis for immune-magnetic isolation of circulating tumor cells. The example process described herein was conducted using two separate chips (named "CTC-iChip1" and "CTC-iChip2"), that were serial (inline) fluid communication.

Device Fabrication

CTC-iChip 1 functioned as the hydrodynamic cell sorting region and included micropost arrays arranged in patterns that enable deterministic displacement of nucleated cells. Silicon was selected as the material from which the post arrays were formed. Glass was utilized as the cover layer, providing both a tight seal (>30 psi pressure range) and optical transparency. Using standard lithography techniques and reactive ion etching, the pillars were fabricated in a silicon substrate, and formed to have depths on the order of 150 μm and pillar height to width aspect ratios of up to 50:1. An example post array fabricated according to this technique is shown in FIG. 9B. In particular, the posts are "egg shaped," and are characterized by a 32 μm gap between adjacent posts, as well as a 1.7° slope between neighboring rows. The top surface of each post has a maximum length of 24 μm and a minimum length of 17 μm. The period between adjacent posts is 56 μm. These array properties yield a 4 μm critical deflection diameter for the microarray.

A custom-made manifold was fabricated to hold the CTC-iChip 1 during the experiment and provide a leak-free interface between the tubing that coupled the CTC-iChip 1 to CTC-iChip 2 and the microfluidic channels of the hydrodynamics sorting region. The main body was composed of a top piece and a bottom piece, each milled from polycarbonate, which were screwed together. The bottom piece had (1) chambers for incoming and outgoing fluids, (2) O-ring grooves around the chambers, and (3) fluidic channels that connect the chambers to (4) short stainless steel tube fittings for connecting silicone tubing.

CTC-iChip2 was produced using a mold of PDMS. The mold was fabricated by first etching the microfluidic channel design into a silicon master using soft-lithography with SU-8 and a mask. Uncured PDMS was then poured onto the mold and cured at 65° C. for about 8 hours. The PDMS containing the outline of the channels then was bonded to a glass substrate. For each device, the PDMS was treated with $O_2$ plasma prior to bonding to the substrate. The outline of the fluidic channel design that was used is shown in FIG. 6, and included two fluidly coupled deflection stages.

A custom made manifold also was fabricated to hold the CTC-iChip2 and the two magnet arrays (i.e. one magnet array on the PDMS and one magnet array on the glass cover). The manifold was composed of a top piece and a bottom piece with chambers for receiving the CTC-iChip2 and magnets. The pieces were secured together using screws.

Figure 11C:
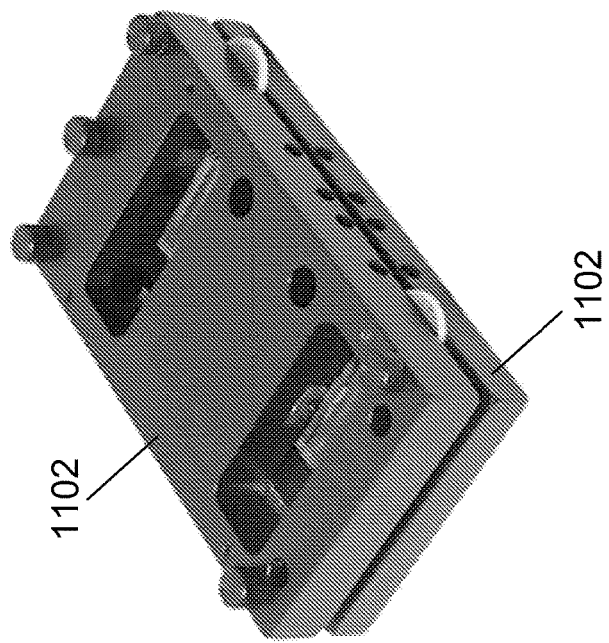
FIGS. 11A-11C are photographs of a manifold for securing magnets to a substrate and microfluidic cover channel.
Figure 11A:
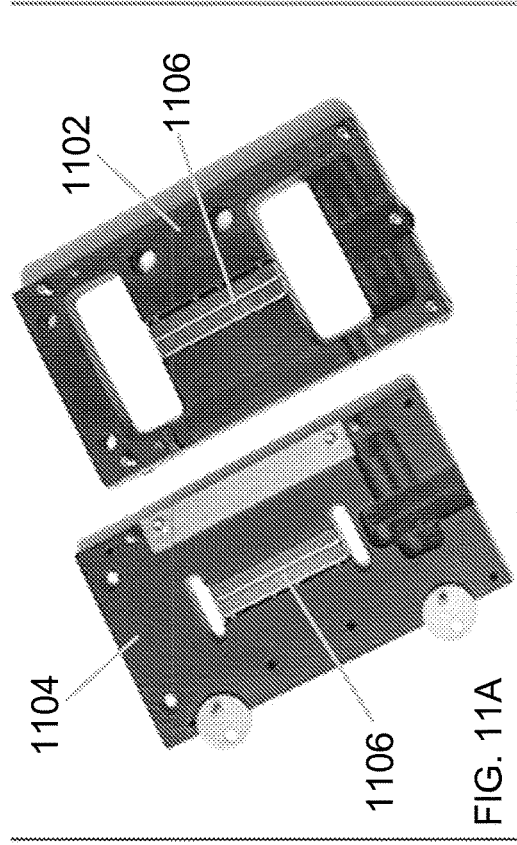
Figure 11B:
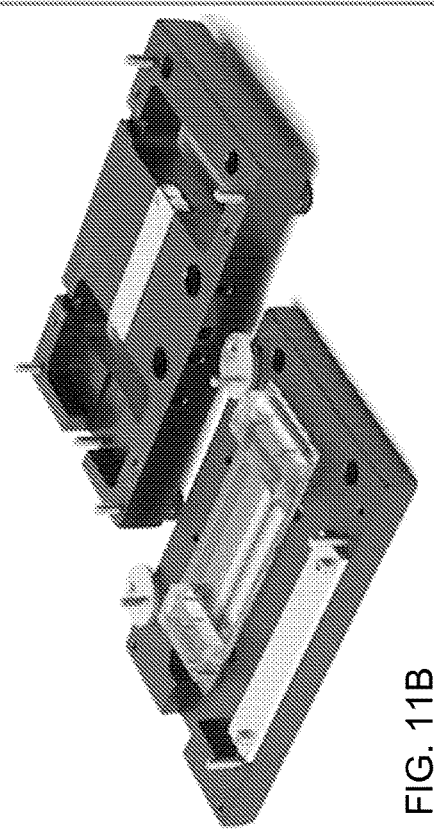

FIG. 11A is a photograph of the top manifold piece 1102 and the bottom manifold piece 1104. As shown in FIG. 11A, an array of two magnets 1106 is positioned in a cavity of each manifold piece. FIG. 11B is a photograph of the bottom manifold piece and the top manifold piece, where the CTC-iChip2 device 1108 is aligned on top of the magnets of the bottom manifold piece. FIG. 11C is a photograph showing the top manifold piece 1102 secured to the bottom manifold piece 1104. The CTC-iChip2 device is positioned between the top and bottom manifold pieces.

Cell Labeling

Micron-sized paramagnetic beads were functionalized with antibodies to target cells of interest and then added to a suspension containing cells expressing the antigen of interest. In particular, the WBC population in the blood sample was labeled by first introducing magnetic-bead free biotinylated CD45 and CD66b antibodies into the sample and subsequently attaching the magnetic beads to the WBC. Blood containing the labeled WBCs was prepared as follows.

First about 200 μL of blood sample from a donor was aliquot into an Eppendorf tube. A complete blood count (CBC) was then performed. The amount of antibody and magnetic beads required were calculated based upon the donor's WBC count and the volume of blood to be run using the following parameters: CD45: 50 fg/WBC; CD66b: 37.5 fg/WBC; and 125 beads/WBC. The donor blood was spiked with cancer cells grown in vitro. In particular, VM164, MB231, PC9, PC3-9, SKBR3 and LBX1 cell lines were used to represent the different types of tumor cells that occur in patients. Prior to spiking, the cell lines were stained with CellTracker® (Invitrogen) and counted using a hemocytometer and an epifluorescence microscope. The number of cells added to the blood sample was approximately 1,000 cancer cells/mL blood. The desired blood volume was then aliquot into a PBS rinsed vacutainer. The calculated volumes of CD45 and CD66b antibodies were then added to whole blood. The sample was pipetted up and down at least 10 times with a 1 ml pipette to fully mix the antibody and blood, and then incubated for 20 minutes. Subsequently the calculated amount of 1 micron diameter magnetic beads (Dynabeads® MyOne® Streptavidin T1 magnetic beads from Invitrogen) were pipetted into the sample and incubated for 20 minutes.

Buffer Preparation

A pluronic running buffer was prepared as follows. First, 2.5 grams of Kolliphor-P188 was weighed out and placed in an empty Nalgene® bottle (250 mL). 250 mL of 1× PBS was then transferred into the Nalgene bottle. A stir bar was placed in the Nalgene bottle, and the bottle was placed on a magnetic stirrer for 20 minutes. The solution was filtered through a Nalgene Filtration System with a 250 ml receiver, and then degassed using ultrasonic bath or a vacuum system.

Device Operation

Figure 12:
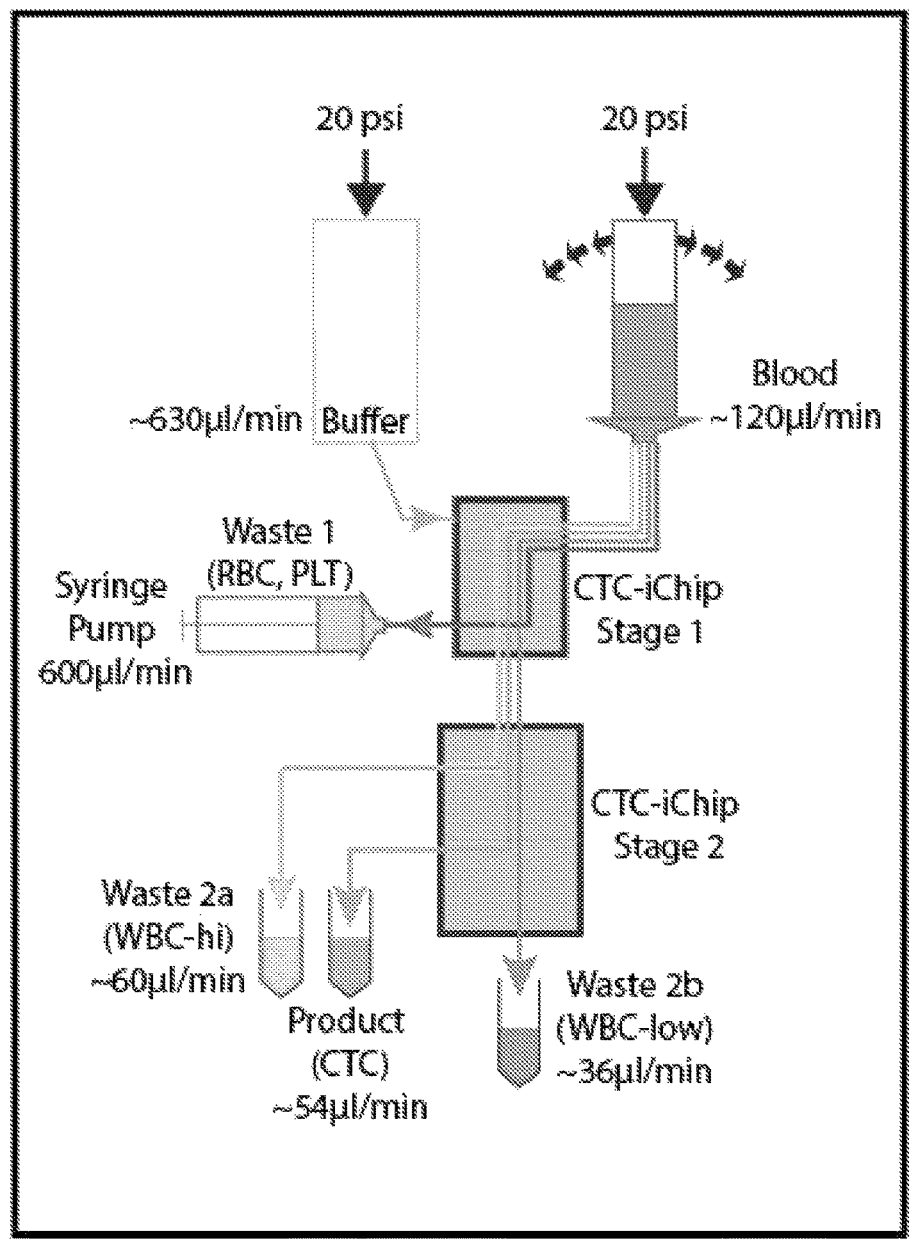
FIG. 12 is a schematic illustrating a fluidic system for sorting cells from a fluid sample.

The CTC-iChip1 and CTC-iChip2 were arranged as shown in FIG. 12. As shown in that schematic, both the blood sample and the buffer solution were input to the CTC-iChip1 via tubing. A constant pressure of 20 psi was applied to both the buffer and blood. CTC-iChip1 separated the magnetically labeled WBCs and the non-labeled CTCs from whole blood. Purified nucleated cell suspension exited from bottom outlet and was transferred to CTC-iChip2 using tubing. The rest of the blood, which was diluted with buffer, was collected in a 60 mL syringe at a rate of 600 μl/min controlled using a syringe pump running in withdrawal mode ("Waste 1"). Once the nucleated cell suspension reached CTC-iChip2, the chip separated the non-labeled CTCs from WBCs in two stages. The output containing highly bead labeled WBCs (i.e., having a high magnetic moment) were collected in a tube labeled "Waste 2a" at a rate of about 64 μL/minutes. Sparsely bead labeled cells (i.e., having a low magnetic moment) were collected in a tube labeled "Waste 2b" at the bottom of the manifold at a rate of about 36 μL/minutes. The product containing isolated CTCs were collected in a tube labeled "Product" at a rate of about 54 μL/minutes.

Results

The CTC-iChip2 described above performed magnetic separation in two serial stages. In the first stage, cells were travelling at approximately 50 mm/second and were sorted at a rate of approximately 10,000 nucleated cells/second and a magnetic sensitivity of about 7 magnetic beads/WBC. This stage was designed to be extremely robust and resistant to aggregations of magnetic beads and WBCs while still having a sufficiently large magnetic gradient to remove 99.9% of WBCs. Bead-labeled cells were deflected toward the center of the flow channel, rather than against a sidewall where they may accumulate and form plaques. Cells that were not deflected in the first stage (i.e., CTCs and WBCs with few beads) continued to the second stage, which included two parallel microfluidic channels (see FIG. 6) in which cells traveled at approximately 30 mm/second and were sorted at a rate of approximately 10-20 nucleated cells/second. The second stage had greater residence time and a larger magnetic field gradient than the first stage, which gave the second stage (and the device as a whole) a magnetic sensitivity of about 2 magnetic beads/WBC. Deflecting bead-labeled cells towards the center of the flow channel rather than the sidewalls prevented generation of aggregates, which upon break-off, may be collected in the product and reduce purity.

Figures 13A, 13B:
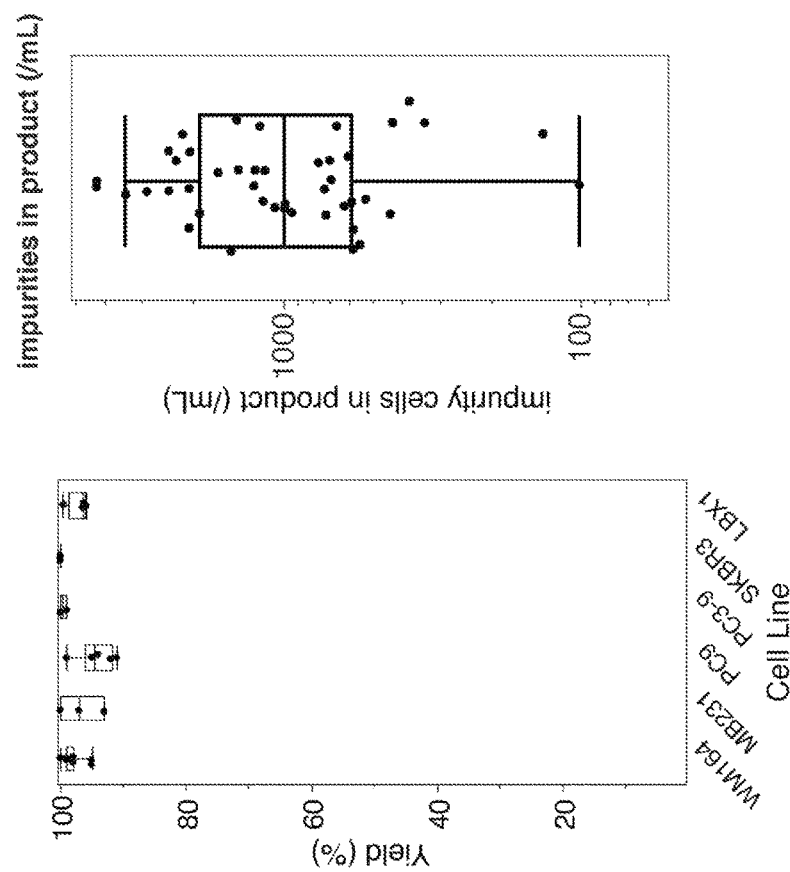
FIG. 13A is a plot that shows cell yield after application of cell sorting based in part on magnetophoresis for different cancer cell lines.
FIG. 13B is a logarithmic plot of the number of white blood cell impurities after application of cell sorting based in part on magnetophoresis.

The percent yield of cancer cells was determined by counting the product using a Nageotte chamber, which is designed to count cells in dilute suspensions. The average yield of the experimental dataset was about %97±2.7%, showing almost complete target cell recovery, regardless of the cell type. FIG. 13A is a plot that shows cell yield for the different cancer cell lines. The number of WBC impurities in the product was also analyzed. In particular, we used immunofluorescence staining with anti-CD45 antigen to count WBCs that carried over into the product. The mean WBC carryover was 1200±900 WBC/mL in all sorted blood samples. The WBC depletion from the blood sample was calculated to be 3.8±0.36 log (average sorted blood volume was 6.8 mL, number of trials "N"=43). FIG. 13B is a plot of the WBC carryover for the different trials. Accordingly, as can be seen from the results in FIGS. 13A-13B, the magnetophoresis device, as described herein, is suitable for separating desired analytes from a fluid sample with little or no plaque formation, and little carryover of undesired analytes into the final product.

Once the clinical blood sample is sorted, a variety of pathological, immunological or molecular analyses are possible (see "Applications" section). For enumerating CTCs from clinical blood samples, immunofluorescence microscopy can be performed using antibodies against CTC markers (i.e. cytokeratins) in one color, WBC markers (i.e., CD45) in another and 4',6-diamidino-2-phenylindole (DAPI) as nuclear marker. Automated immunofluorescence microscopy yields the number of CTCs in the enriched clinical sample, which can be converted to the number of CTCs/mL of blood analyzed. When this procedure is repeated for a patient, their number of CTCs/mL of blood can be tracked.

Example 2

Examining Device Robustness and Effectiveness

Additional studies also were performed using copies of the CTC-iChip1 and CTC-iChip2 designs described above in Example 1. In particular, the CTC-iChip1 and CTC-iChip2 systems were fabricated (as described in Example 1) for performing similar but separate experiments at three different research sites so as to review the robustness and effectiveness of deterministic lateral displacement, inertial focusing and magnetophoresis techniques (as combined in the CTC-iChip configuration) for isolating circulating tumor cells from whole blood samples and the depletion of white blood cells. The three research sites are referenced below as "JRD," "JDX," and "MGH." Blood samples were prepared and processed for each experiment using the following workflow: (a) blood sample acquisition from donors and sample preparation, (b) isolation of CTCs using the iChip configuration (CTC-iChip1 and CTC-iChip2) as fabricated above, (c) plating of the isolated cells subsequent to isolation, (d) staining of the plated cells following plating, and (e) enumeration of the number of isolated cells. Three basic tests were performed with each device: a study of absolute recovery—linearity; a study of absolute recovery—between donors; and a study of absolute recovery—within a donor. The purpose of the absolute recovery—linearity test was to demonstrate that the effectiveness of the CTC recovery is invariant with respect to the total number of cells input to the device. The purpose of the absolute recovery—within a donor test was to analyze the consistency of the device effectiveness with respect to CTC recovery across different samples from the same patient. The purpose of the absolute recovery—between donors test was to analyze the consistency of the device effectiveness with respect to CTC recovery across different samples from different patients. A discussion of the protocol for each test and the results is set forth below.

Blood Collection and Handling

For the experiments, blood was drawn from each donor and collected into plastic $K_2EDTA$ vacutainers (10 ml). Vacutainers with less than 6 ml were discarded. Following draw, each tube was inverted 8-10 times to ensure adequate distribution of the anticoagulant. Vacutainers were then pooled up to a volume of 50 ml in a polypropylene 50 ml tube and mixed via inversion 8-10 times to ensure adequate mixing. For labeling, the WBC population in the blood sample was labeled by first introducing magnetic-bead free biotinylated CD45 and CD66b antibodies into the samples and subsequently attaching the micron-sized paramagnetic beads to the WBC.

All experiments also utilized a model circulating tumor cell surrogate (mock sample) consisting of a pre-fixed BT474 cancer cell line stabilized in a matrix of phosphate buffered saline with 5% bovine serum albumin and 0.1% sodium azide. The stock concentration of the control cell lot used for all experiments was 11,960±1,004 cell/ml. Each mock sample contained blood volume of 6 ml and a spike volume for the BT474 cells of 100 μl, incubated with 108 μl of depletion antibodies and 0.72 ml of magnetic beads.

Absolute Recovery—Linearity

For the absolute recovery—linearity experiments, the sample preparation workflow was set forth as follows. Blood from a single donor was pooled and split into six aliquots, one for each condition (five samples spiked with the CTC cell line and an unspiked buffer control). Following pooling (see above), precisely 6 ml of blood was pipetted into each of seven polypropylene 15 ml conical tubes prior to mock sample preparation. Six tubes were utilized for the experiment and the seventh kept as a back up. Next, a stock of fixed control cells was serially diluted 4× in phosphate buffered saline with 1% F68 to produce the requisite number of cells for each condition in a 100 μL volume. Isolation using CTC-iChip1 and CTC-iChip2 was performed in two rounds, typically Round 1 in the morning and Round 2 in the afternoon. Mock samples were stored static at room temperature prior to isolation.

Absolute Recovery—Between Donors

For the absolute recovery—between donor experiments, the sample preparation workflow was set forth as follows. Blood from three independent donors was pooled separately; two aliquots were processed for each donor. Following pooling, precisely 6 mL of blood was pipetted into each of three polypropylene 15 mL conical tubes prior to mock sample preparation. Two tubes were utilized for the experiment and the third kept as a back up. Next, a stock of fixed control cells was diluted 4× in phosphate buffered saline with 1% F68 to produce the requisite number of cells for each condition in a 100 μL volume. Isolation using CTC-iChip1 and CTC-iChip2 was performed in two rounds, typically Round 1 in the morning and Round 2 in the afternoon. Mock samples were stored static at room temperature prior to isolation.

Absolute Recovery—within a Donor

For the absolute recovery—within a donor, the sample preparation workflow was set forth as follows. Blood from a single donor was pooled and split to support each condition (six, nominally identical replicates). Following pooling, precisely 6 mL of blood was pipetted into each of seven polypropylene 15 mL conical tubes prior to mock sample preparation. Six tubes were utilized for the experiment and the seventh kept as a back up. Next, a stock of fixed control cells was diluted 4× in phosphate buffered saline with 1% F68 to produce the requisite number of cells for each condition in a 100 μL volume. Isolation using CTC-iChip1 and CTC-iChip2 (as described in "Device Operation" under Experiment 1 above) was performed in two rounds, typically Round 1 in the morning and Round 2 in the afternoon. Mock samples were stored static at room temperature prior to isolation.

Isolation

Isolation was performed within 5 hours of blood draw. The first step in the isolation process is the exposure of the mock sample to the depletion antibodies (108 µL). Prior to this point the samples were kept static; after this point the samples were mixed until isolation was completed. The second step in the isolation process is the exposure of the mock sample to the magnetic beads (720 µL). The depletion antibody and bead incubation steps were required to be conducted for the prescribed minimum of 30 minutes, but not for greater than 45 minutes. Precisely 6 mL of mock sample exposed to depletion reagents was then transferred via pipette into the sample reservoir on the isolator (i.e., the CTC-iChip1 and CTC-iChip2) and processed to completion. Product fractions were only massed; no sample volume was removed for characterization of any kind prior to plating.

Plating

Plating was performed within 30 minutes of isolation of the cells. The isolated cells were split evenly and plated across two slides. Following plating and fixation, slides were segregated and stored refrigerated (298° C.) in phosphate buffered saline.

Staining

Staining was performed within 24 hours of isolation of the cells. Following staining and mounting, slides were protected from light and stored refrigerated (298° C.).

Scanning

Scanning was performed within 72 hrs of staining completion. Scanning was done in two rounds for each experiment, striping across conditions whenever possible. Each slide was scanned in its entirety with a 10× objective to provide quantitative end-to-end data for CTC recovery and WBC depletion. A subset of randomly selected targets from each primary Vectra class was also scanned using a 60× objective.

Enumeration

Enumeration was performed within 72 hours of scanning completion.

Endpoint Analysis

The primary endpoints for the studies (CTC recovery, Log WBC depletion, and nucleated cell carryover) are defined as follows. The expected tumor cell number is the number of spike CTCs expected based on lot characterization of spike stock solution and dilution (where relevant), adjusted for partial transfer following exposure to depletion reagents. The observed tumor cell number is the total of verified target cells from both slides using the 10× objective including the following Vectra classes: NucCTCs (a machine vision category for the CTCs). The CTC recovery percentage is 100 times (the observed tumor cell number)/(the expected tumor cell number). The WBCs processed is the complete blood count measurement of WBC/mL times 5.2 mL blood processed. Nucleated cells detected is the total of verified 10× WBCs and nuclei from both slides (excluding target cells), including the following Vectra classes: BrightWBCs, WeakWBCs, NucDuals, WeakNucDuals, BareWBCs (machine vision categories for white blood cells). Nucleated Cell Carryover is the nucleated cells detected divided by 5.2 mL blood processed. The Log WBC depletion is the Logio (WBCs processed/nucleated cells detected).

Results

The experiments were performed over a period of 20 days. The overall yield/reliability of the system design corresponds to the percent of individual blood samples that pass completely through the device (i.e., full volume processed) without any issues, such as blockage leaks, etc. For the experiments that were performed, an overall yield/reliability of 79% was obtained, thus indicating that the device design was sufficiently robust and did not experience detrimental clogging due to the development of plaques. The overall linearity, which corresponds to the expected number of CTCs collected versus the observed number of CTCs collected was 1.05, which is within ±0.05 of the ideal 1.00 linearity. The overall analytical specificity/purity, which corresponds to the total number of background cells detected for each milliliter of blood had a median value of 148 cells/mL.

Table 1 summarizes the functional performance of the combined CTC-iChip1 and CTC-iChip2 for depleting WBCs from a blood sample in terms of nucleated cell carryover, nucleated cell/7.5 mL and log WBC depletion across the different sites and experiments, where n is the number of runs and CV is the coefficient of variation. The fewer number of nucleated cells carried over, the better the device performance. The log WBC depletion is a measure of WBC depletion relative to the input number of cells. The data in Table 1 demonstrates that the combination of deterministic lateral displacement, inertial focusing, and magnetophoresis is capable of achieving a substantial amount of white blood cell depletion from whole blood. The strength of the results is enhanced given that the data was collected across many individual donors (24) and using devices developed at three independent research sites.

TABLE 1

| Endpoint | n | Mean | Stand Deviation | CV | Median | Min | Max |
| --- | --- | --- | --- | --- | --- | --- | --- |
| Nucleated Cell Carryover (cell/mL blood) | 96 | 239 | 345 | 145 | 148 | 28 | 2962 |
| Nucleated cell/7.5 mL | 96 | 1789 | 2586 | 145 | 1106 | 210 | 22215 |
| Log WBC Depletion | 96 | 4.5 | 0.3 | 7 | 4.5 | 3.4 | 5.3 |

Figure 16:
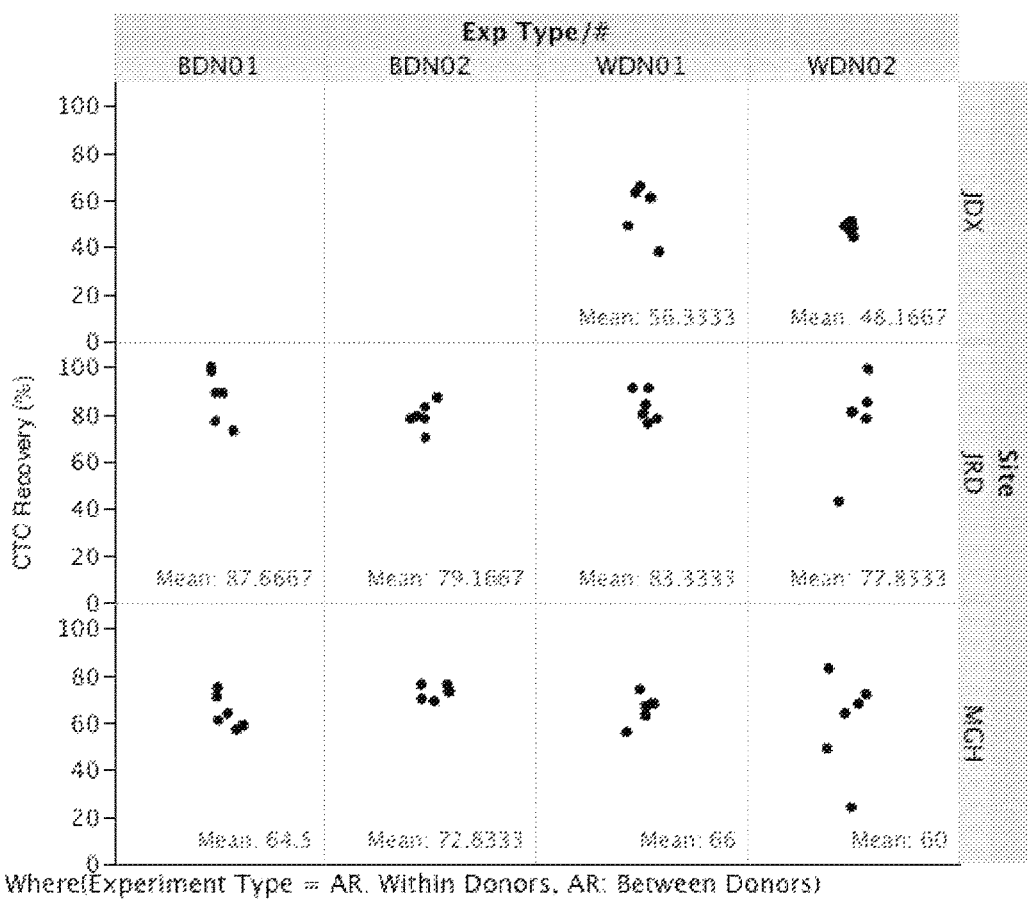
FIG. 16 is a plot of the circulating tumor cell (CTC) recovery results

FIG. 16 is a plot of the CTC recovery results for the Within Donor and the Between Donors tests for the different testing sites. Table 2 summarizes the CTC recovery results across the different testing sites.

TABLE 2

| Endpoint | n | Mean | Stand Deviation | CV | Median | Min | Max |
| --- | --- | --- | --- | --- | --- | --- | --- |
| CTC Recovery (%) (JRD) | 34 | 92 | 31 | 34 | 85 | 43 | 222 |
| CTC Recovery (%) (JDX) | 22 | 61 | 19 | 31 | 59 | 38 | 124 |
| CTC Recovery (%) (MGH) | 34 | 62 | 17 | 27 | 68 | 19 | 99 |
| CTC Recovery (%) (All sites) | 90 | 73 | 28 | 38 | 72 | 19 | 222 |

Figure 17:
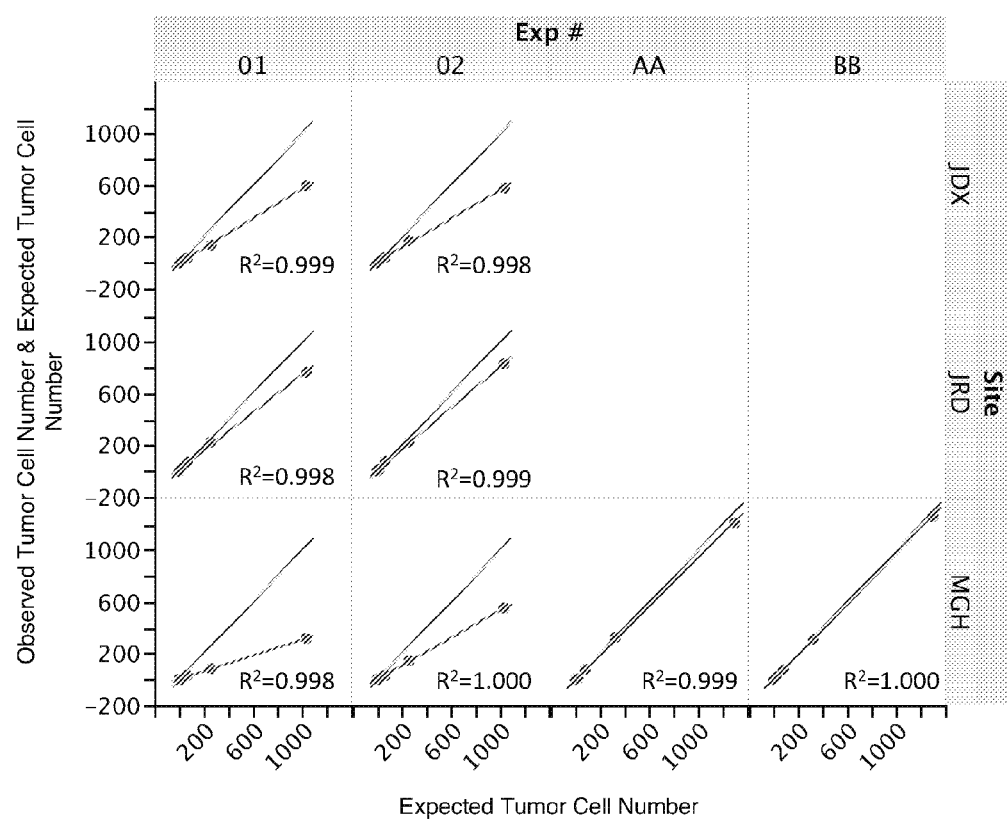
FIG. 17 is a plot of the observed circulating tumor cell number versus the expected circulated tumor cell number.

FIG. 17 is a plot of the observed circulating tumor cell number versus the expected circulated tumor cell number for the different experiments performed at each site. Two lines are shown for each experiment: a solid upper line corresponding to the ideal case of 1:1 correlation between observed and expected results and a lower line fitted to actual results. As shown in these results, the combination of deterministic lateral displacement, inertial focusing, and magnetophoresis is capable of achieving a relatively high recovery of CTCs (mean of 73% and median of 72% across testing sites) from whole blood.

Other Embodiments

It is to be understood that while the invention has been described in conjunction with the detailed description thereof, the foregoing description is intended to illustrate and not limit the scope of the invention, which is defined by the scope of the appended claims.

For example, in some implementations, the microfluidic device is constructed to include a single magnet above the microfluidic channel and a single magnet below the microfluidic channel, where the two magnets are aligned such that the magnetic flux gradient profile formed between the magnets includes a first maxima and a second maxima that bound a local minimum. In addition, the top magnet has a polarization orientation that is flipped with respect to the polarization orientation of the bottom magnet. This is called a "dipole" configuration. In such an implementation, the peak lateral gradient may not be as large or symmetric about the gradient zero-point as in the configurations where the top and bottom magnet arrays each include two or more magnets.

Figure 14:
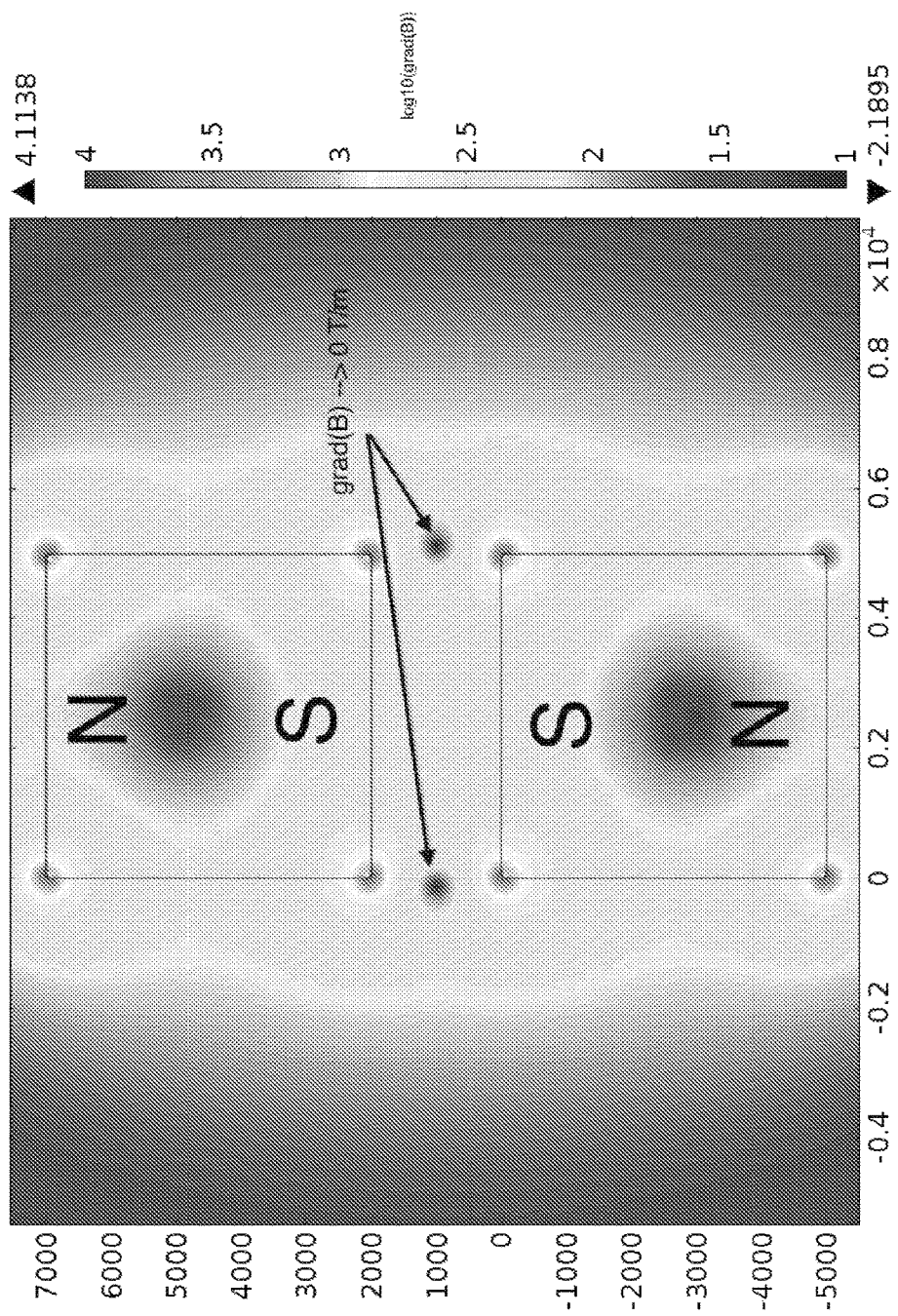
FIG. 14 is a heat map plot of the absolute value of the magnetic flux gradient profile for a dipole magnet configuration.

FIG. 14 is a heat map plot of the absolute value of the magnetic flux gradient profile for a microfluidic device configuration that includes a single top magnet and a single bottom magnet. For ease of viewing, the microfluidic channel between the two magnets is not shown. As can be seen in FIG. 14, this configuration includes two points where the magnetic flux gradient reaches zero. The microfluidic channel would be positioned such that the flux zero-point location is in the channel or nearby. As a result, labeled cells traversing through the channel would be deflected by the resulting magnetic forces toward the zero-point location.

Figure 15:
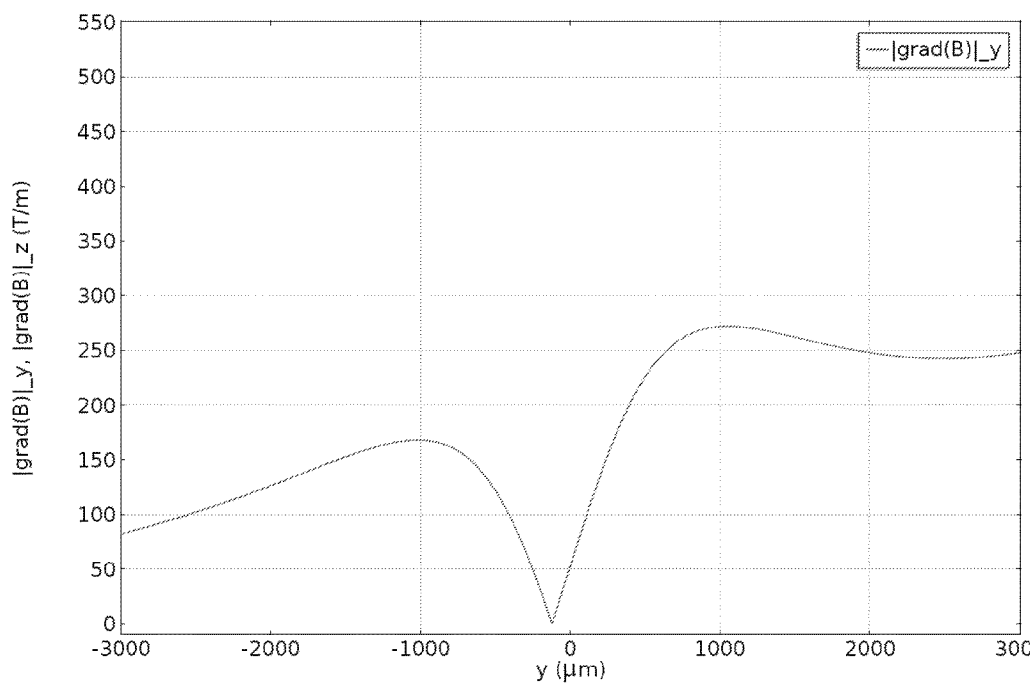
FIG. 15 is a plot that shows a simulation of the magnitude of a magnetic flux gradient profile for a dipole magnet configuration.

FIG. 15 is a plot of the absolute value of the magnetic flux gradient profile for the configuration containing a single top magnet and a single bottom magnet, in which only one of the local minima in flux gradient is shown.

Other aspects, advantages, and modifications are within the scope of the following claims.

What is claimed is:

1. A microfluidic device comprising:
a microfluidic channel;
a first array of two or more magnets arranged above the microfluidic channel,
wherein each magnet in the first array has a magnetic pole orientation that is opposite to a magnetic pole orientation of an adjacent magnet in the first array; and
a second array of two or more magnets arranged beneath the microfluidic channel and facing the first array of two or more magnets;
wherein each magnet in the second array has a magnetic pole orientation that is opposite to a magnetic pole orientation of an adjacent magnet in the second array,
wherein the first array is aligned with respect to the second array such that magnetic fields emitted by the first array and the second array generate a magnetic flux gradient profile that extends through the microfluidic channel, and wherein an absolute value of the magnetic flux gradient profile comprises a first peak and a second peak that bound a local minimum in the magnetic flux gradient profile, and wherein the local minimum is located within the microfluidic channel or less than 5 mm away from a wall of the microfluidic channel, and wherein the magnetic flux gradient profile having the first peak, the second peak and the local minimum extends transverse to a central longitudinal axis of the microfluidic channel, and
wherein the microfluidic channel is a first microfluidic channel, the device further comprises a second microfluidic channel arranged adjacent to the first microfluidic channel, and the magnetic flux gradient profile extends through both the first microfluidic channel and the second microfluidic channel.

2. The microfluidic device of claim 1, wherein a first interface between two magnets in the first array is substantially aligned with a second interface between two magnets in the second array.

3. The microfluidic device of claim 1, wherein each magnet in the first array has a magnetic pole orientation that is opposite to a magnetic pole orientation of a corresponding magnet in the second array.

4. The microfluidic device of claim 1, wherein at least one of the first peak in the magnetic flux gradient and the second peak in the magnetic flux gradient occurs within the first microfluidic channel.

5. The microfluidic device of claim 1, wherein
the first array comprises more than two magnets;
the second array comprises more than two magnets; and
the absolute value of the magnetic flux gradient profile comprises at least two local minima, wherein at least one of the local minima is located within the first microfluidic channel.

6. The microfluidic device of claim 1, wherein the second microfluidic channel is in fluid communication with the first microfluidic channel.

7. The microfluidic device of any one of claim 1, further comprising:
a first output channel fluidly coupled to an output of the second microfluidic channel; and
a second output channel fluidly coupled to the output of the second microfluidic channel, wherein the local minimum is aligned with a longitudinal axis of the first output channel or of the second output channel.

8. A method of sorting a target analyte using the microfluidic device of claim 1, the method comprising:
flowing a fluid sample through the first microfluidic channel, the fluid sample comprising a target analyte and one or more magnetic particles; and
exposing, during operation of the microfluidic device, the fluid sample to the magnetic flux gradient profile, wherein the magnetic flux gradient deflects the one or more bound magnetic particles toward the local minimum.

9. The method of claim 8, wherein the fluid sample comprises one or more second particles in addition to the target analyte, and
wherein the one or more magnetic particles are bound to the one or more second particles such that the magnetic flux gradient deflects the second particles with the one or more magnetic particles away from an initial fluid flow trajectory of the fluid sample without deflecting the target analyte, and wherein the method further comprises collecting the target analyte from the fluid flow trajectory at an output of the first microfluidic channel subsequent to the deflection of the one or more second particles.

10. The method of claim 8, wherein the one or more magnetic particles are bound to the target analyte such that the magnetic flux gradient deflects the target analyte with the one or more magnetic particles away from an initial fluid flow trajectory of the fluid sample, and wherein the method further comprises collecting the target analyte at an output of the first microfluidic channel.

11. A method of sorting analytes in a microfluidic device, wherein the microfluidic device comprises a magnetophoresis region, the method comprising:
flowing a fluid sample containing a mixture of a plurality of first analytes and a plurality of second analytes into a microfluidic channel within the magnetophoresis region, wherein, upon entering the microfluidic channel, the plurality of first analytes and the plurality of second analytes flow along one or more common streamlines,
wherein the plurality of second analytes are bound to magnetic particles,
wherein the magnetophoresis region comprises (1) a first array of two or more magnets arranged above the microfluidic channel and (2) a second array of two or magnets arranged beneath the microfluidic channel such that each magnet in the first array faces a corresponding magnet in the second array,
wherein each magnet in the first array has a magnetic pole orientation that is opposite to a magnetic pole orientation second of an adjacent magnet in the first array and that is opposite to a magnetic pole orientation of a facing magnet within the second array,
wherein the first array is aligned with respect to the second array such that magnetic fields emitted by the first array and the second array generate a magnetic flux gradient profile that extends through the microfluidic channel,
wherein the magnetic flux gradient profile within the magnetophoresis region deflects the plurality of second analytes from the one or more common streamlines in the fluid sample without deflecting the plurality of first analytes from the one or more common streamlines,
wherein an absolute value of the magnetic flux gradient profile comprises a first peak and a second peak that bound a local minimum in the magnetic flux gradient profile, and
wherein the local minimum is located within the microfluidic channel in the magnetophoresis region and at least 50 µm away from each microfluidic channel wall in the magnetophoresis region.

12. The method of claim 11, wherein the microfluidic device further comprises a hydrodynamic particle sorting region arranged upstream from and in fluid communication with the magnetophoresis region and an inertial focusing region arranged upstream from and in fluid communication with the magnetophoresis region, the method further comprising:
prior to flowing the fluid sample into the magnetophoresis region, introducing the fluid sample into the hydrodynamic particle sorting region to separate a first portion of the first analytes from the fluid sample, wherein the remaining fluid sample from the hydrodynamic sorting region comprises the plurality of second analytes and a second portion of the first analytes and is passed to the magnetophoresis region; and prior to flowing the remaining fluid sample into the magnetophoresis region, flowing the remaining fluid sample from the hydrodynamic region into the inertial focusing region, wherein the inertial focusing region focuses analytes in the remaining fluid sample into the one or more common streamlines.

13. The method of claim 11, wherein the first plurality of analytes is not bound to magnetic particles.

14. The method of claim 11, wherein the microfluidic device further comprises a first inertial focusing region and a second inertial focusing region, wherein each inertial focusing region is fluidly coupled to a common input port of the magnetophoresis region, the method further comprising:
flowing a first fluid sample portion into the first inertial focusing region, wherein the first inertial focusing region focuses analytes in the first fluid sample portion into a first streamline; and
flowing a second fluid sample portion into the second inertial focusing region, wherein the second inertial focusing region focuses analytes in the second fluid sample portion into a second streamline,
wherein both the first and second streamlines enter the common input port of the magnetophoresis region.

15. The method of claim 14, wherein the magnetic flux gradient profile within the magnetophoresis region deflects the second plurality of analytes from the first and second fluid streamlines into a separate third fluid streamline.

16. The method of claim 15, further comprising, subsequent to deflecting the second plurality of analytes:
directing the first, second, and third fluid streamlines to first, second, and third output channels, respectively;
collecting, at the first and second output channels, the first plurality of analytes; and
collecting, at the third output channel, the second plurality of analytes.

17. A method of sorting analytes in a microfluidic device comprising a first microfluidic channel arranged in fluid communication with a second microfluidic channel, wherein a magnetic flux gradient extends through both the first and second microfluidic channels, the method comprising:
introducing a fluid sample containing a first plurality of analytes into the first microfluidic channel,
wherein the first plurality of analytes are bound to magnetic particles, and wherein the magnetic flux gradient profile within the first microfluidic channel deflects a first portion of the first plurality of analytes from a streamline within the fluid sample; and
flowing a remaining fluid sample from the first microfluidic channel into the second microfluidic channel, wherein the magnetic gradient profile deflects a second portion of the first plurality of analytes from a streamline in the remaining fluid sample, and
wherein the absolute value of the magnetic flux gradient profile comprises a first peak and a second peak that bound a local minimum in the magnetic flux gradient profile, the local minimum being located within one of the first microfluidic channel or the second microfluidic channel, and wherein either the first peak or the second peak is located within the other one of the first microfluidic channel or the second microfluidic channel.

18. The method of claim 17, wherein the remaining fluid sample comprises a second plurality of analytes that are not bound to magnetic particles, the method further comprising:
collecting the second plurality of analytes at a first output of the second microfluidic channel; and collecting the second portion of the first plurality of analytes at a second output of the second microfluidic channel.

\* \* \* \* \*

UNITED STATES PATENT AND TRADEMARK OFFICE
CERTIFICATE OF CORRECTION

PATENT NO. : 10,202,577 B2  
APPLICATION NO. : 15/029789  
DATED : February 12, 2019  
INVENTOR(S) : Philipp S. Spuhler et al.

Page 1 of 1

It is certified that error appears in the above-identified patent and that said Letters Patent is hereby corrected as shown below:

In the Claims

Column 36, Claim 7, Line 40:
Delete "of any one of" and Insert --of--

Signed and Sealed this
Twenty-sixth Day of March, 2019

Andrei Iancu
*Director of the United States Patent and Trademark Office*